United States Patent
Volkar et al.

(10) Patent No.: US 11,931,555 B2
(45) Date of Patent: Mar. 19, 2024

(54) INDEPENDENT WORKFLOW AWARE USER INTERFACES FOR POWER INJECTOR SYSTEM OPERATION

(71) Applicant: BAYER HEALTHCARE LLC, Whippany, NJ (US)

(72) Inventors: John Volkar, Thornleigh, PA (US); Corey Kemper, Pittsburgh, PA (US); Samantha Parker, Pittsburgh, PA (US); James Hoon Yoo, Baulkham Hills (AU); Leona Mulcahy, Epping (AU); Michael Brooks, Croydon Park (AU); Richard Sokolov, Earlwood (AU)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 17/386,897

(22) Filed: Jul. 28, 2021

(65) Prior Publication Data
US 2021/0353870 A1     Nov. 18, 2021

Related U.S. Application Data

(62) Division of application No. 17/043,808, filed as application No. PCT/US2019/026486 on Apr. 9, 2019, now Pat. No. 11,090,440.

(Continued)

(51) Int. Cl.
*G06F 3/04847*     (2022.01)
*A61M 5/315*     (2006.01)
(Continued)

(52) U.S. Cl.
CPC ..... *A61M 5/31546* (2013.01); *G06F 3/04847* (2013.01); *G09G 5/12* (2013.01);
(Continued)

(58) Field of Classification Search
CPC ... A61M 5/31546; G06F 3/04847; G09G 5/12
See application file for complete search history.

(56) References Cited

U.S. PATENT DOCUMENTS 8,108,464 B1 *   1/2012   Rochelle ................. H04L 51/00
                                                                                       709/204
10,758,673 B2    9/2020   Hyde et al.
(Continued)

FOREIGN PATENT DOCUMENTS

WO     2007062315 A2     5/2007

OTHER PUBLICATIONS

Bayer., "MRXperion OpManual-3038591 Rev H Feb. 13, 2018", Feb. 13, 2018.

(Continued)

*Primary Examiner* — William L Bashore
*Assistant Examiner* — Gregory A Distefano
(74) *Attorney, Agent, or Firm* — James R. Stevenson; Aaron Mace

(57) ABSTRACT

A power injector system having a power injector for enabling delivery of fluid in an injection procedure to be performed on a patient may include one or more processors; a first user interface; and a second user interface. The first user interface and the second user interface may be configured to accept a plurality of user inputs associated with control of a plurality of operations of the power injector system and display information associated with the plurality of operations. One of the first user interface and the second user interface may be proximate to the power injector and the other may be remote from the power injector. The one or more processors may be programmed and/or configured to independently control the first user interface and the second (Continued)

user interface based on a first user input and a next user input received from the first user interface and/or the second user interface.

19 Claims, 13 Drawing Sheets

Related U.S. Application Data

(60) Provisional application No. 62/655,360, filed on Apr. 10, 2018.

(51) Int. Cl.
*G09G 5/12* (2006.01)
*A61M 5/00* (2006.01)

(52) U.S. Cl.
CPC ....... *A61M 5/007* (2013.01); *A61M 2205/502* (2013.01); *A61M 2205/52* (2013.01); *G09G 2354/00* (2013.01); *G09G 2380/08* (2013.01)

(56) References Cited

U.S. PATENT DOCUMENTS

| | | | |
|---|---|---|---|
| 2004/0254533 A1 | 12/2004 | Schriver et al. | |
| 2005/0010447 A1 | 1/2005 | Miyasaka et al. | |
| 2005/0288571 A1* | 12/2005 | Perkins | A61B 5/742 600/407 |
| 2007/0083152 A1 | 4/2007 | Williams et al. | |
| 2009/0076461 A1 | 3/2009 | Susi et al. | |
| 2009/0088731 A1 | 4/2009 | Campbell et al. | |
| 2010/0125174 A1* | 5/2010 | Bevan | G16H 40/67 600/300 |
| 2010/0185183 A1* | 7/2010 | Alme | A61M 5/14276 604/891.1 |
| 2010/0198055 A1 | 8/2010 | Assmann et al. | |
| 2011/0289150 A1* | 11/2011 | Westaway | H04L 67/104 709/205 |
| 2012/0123257 A1 | 5/2012 | Stokes, Jr. et al. | |
| 2012/0323212 A1* | 12/2012 | Murphy | A61M 5/1723 604/151 |
| 2013/0067416 A1 | 3/2013 | Barron et al. | |
| 2013/0172774 A1* | 7/2013 | Crowder | G16H 20/10 600/300 |
| 2014/0113553 A1 | 4/2014 | Brukalo et al. | |
| 2015/0011970 A1 | 1/2015 | Kamen et al. | |
| 2015/0127376 A1 | 5/2015 | Ortenzi et al. | |
| 2016/0113594 A1 | 4/2016 | Koehler et al. | |
| 2016/0133160 A1 | 5/2016 | Packer et al. | |
| 2017/0164917 A1 | 6/2017 | Joerger et al. | |
| 2017/0172527 A1 | 6/2017 | Uber, III | |

OTHER PUBLICATIONS

"International Preliminary Report on Patentability from PCT Application No. PCT/US2019/026486", dated Oct. 22, 2020.
"Mark 7 Arterion Injection System Operation Manual, Rev. Q", Jan. 21, 2017.

* cited by examiner

INDEPENDENT WORKFLOW AWARE USER INTERFACES FOR POWER INJECTOR SYSTEM OPERATION

CROSS-REFERENCE TO RELATED APPLICATION

This application is a divisional of U.S. application Ser. No. 17/043,808, which is a U.S. national phase application under 35 U.S.C. § 371 of PCT International Application No. PCT/US2019/026486, filed Apr. 9, 2019 and claims priority to U.S. Provisional Patent Application No. 62/655,360, filed Apr. 10, 2018, the disclosures of which are hereby incorporated by reference in their entirety.

BACKGROUND

Field

This disclosure relates to systems, methods, and computer program products for power injector system operation.

Description of Related Art

Injecting contrast media into bloodstreams of patients enables visualization of various pathologies through X-ray, computed tomography, magnetic resonance, or other medical-imaging modalities. Contrast delivery is more effective and efficient using a medical device called a "power fluid injector system" that can be programmed to deliver specific amounts of contrast agent at specific flow rates.

Power fluid injector systems include a "head" to which one or two syringes may be connected. For dual syringe injection systems, a technologist will typically fill one of the syringes with contrast media and the other syringe with saline. For each syringe, a drive mechanism within the head is used to drive a plunger within the syringe to push the contrast media and/or saline out of the syringes into tubing attached to a patient's vascular system. Because it may be desirable to minimize the amount of tubing needed, the injector head typically resides near the patient in the scan room where the imaging procedures are performed. The injector head may be mounted on a floor pedestal or from an overhead mount in the scan room. Adjacent to the scan room is the control room in which a "control unit" of the fluid injector system is typically located. The control unit is a computer workstation from which the technologist may not only program the injection protocol including the flow rates and volumes according to which the contrast media and saline will be injected into the patient but also start and stop the injection procedures.

SUMMARY

Provided are systems, devices, products, apparatuses, and/or methods for improving power injector system operation.

According to some non-limiting embodiments or aspects, provided is a power injector system having a power injector for enabling delivery of fluid in an injection procedure to be performed on a patient, the power injector system comprising: one or more processors; a first user interface; and a second user interface, wherein the first user interface and the second user interface are configured to accept a plurality of user inputs associated with control of a plurality of operations of the power injector system, wherein the first user interface and the second user interface are configured to display information associated with the plurality of operations of the power injector system, wherein one of the first user interface and the second user interface is proximate to the power injector and the other of the first user interface and the second user interface is remote from the power injector, wherein the one or more processors are programmed and/or configured to: (a) upon receiving a first user input of the plurality of user inputs and a next user input of the plurality of user inputs from only one of the first user interface and the second user interface, (I) determine from the plurality of operations, based on the first user input and the next user input, a first operation thereof and a next operation thereof that are associated, respectively, with the first user input and the next user input, and control, according to the determination of the first operation and the next operation, the first user interface and the second user interface to display information associated with the first operation, the next operation, and a current operational state of the power injector system; and (b) upon receiving the first user input of the plurality of user inputs and the next user input of the plurality of user inputs from one of the first user interface and the second user interface and the other of the first user interface and the second user interface, respectively, and further: (I) upon determining that the first operation and the next operation associated, respectively, with the first user input and the next user input are of a type that can be performed independently, control, according to the determination, (i) the first user interface and the second user interface to display the information associated with the first operation, the next operation, and the current operational state of the power injector system and (ii) the first user interface and the second user interface to cooperatively accept current user input associated with the current operational state of the power injector system; and (II) upon determining that the first operation and the next operation associated, respectively, with the first user input and the next user input are of a type that can be performed only sequentially, control, according to the determination, the first user interface and the second user interface to synchronize display of, but not mirror, the information associated with the first operation, the next operation, and the current operational state of the power injector system.

In some non-limiting embodiments or aspects, the one or more processors are further programmed and/or configured to: control the first user interface to display the information associated with the first operation, the next operation, and the current operational state of the power injector system in a first visual layout; and control the second user interface to display the information associated with the first operation, the next operation, and the current operational state of the power injector system in a second visual layout different than the first visual layout.

In some non-limiting embodiments or aspects, a third user interface, wherein the third user interface is configured to accept the plurality of user inputs associated with control of the plurality of operations of the power injector system, and wherein the third user interface is configured to display information associated with the plurality of operations of the power injector system.

In some non-limiting embodiments or aspects, the one or more processors are further programmed and/or configured to: control the one of the first user interface and the second user interface and the other of the first user interface and the second user interface to simultaneously accept the first user input of the plurality of user inputs and the next user input of the plurality of user inputs, respectively.

In some non-limiting embodiments or aspects, the first user input and the next user input are associated with a same operational state of the power injector system.

In some non-limiting embodiments or aspects, the first user input and the next user input are associated with different operational states of the power injector system.

In some non-limiting embodiments or aspects, the one or more processors are further programmed and/or configured to: control the first user interface based on information associated with a first patient; and simultaneously control the second user interface based on information associated with a second patient different than the first patient.

In some non-limiting embodiments or aspects, the one or more processors are further programmed and/or configured to: control the one of the first user interface and the second user interface and the other of the first user interface and the second user interface to prevent acceptance of the next user input and the first user input, respectively.

In some non-limiting embodiments or aspects, the current operational state of the power injector system is different than the first operation and the next operation.

In some non-limiting embodiments or aspects, the one or more processors are further programmed and/or configured to: control the second user interface to provide a prompt that requests a user to input the next user input via the first user interface.

According to some non-limiting embodiments or aspects, a computer program product comprising at least one non-transitory computer-readable medium including program instructions that, when executed by at least one processor, cause the at least one processor to: control a first user interface and a second user interface of a power injector system having a power injector for enabling delivery of fluid in an injection procedure to be performed on a patient, wherein the first user interface and the second user interface are configured to accept a plurality of user inputs associated with control of a plurality of operations of the power injector system, wherein the first user interface and the second user interface are configured to display information associated with the plurality of operations of the power injector system, wherein one of the first user interface and the second user interface is proximate to the power injector and the other of the first user interface and the second user interface is remote from the power injector, and wherein the instructions cause the at least one processor to control the first user interface and the second user interface by: (a) upon receiving a first user input of the plurality of user inputs and a next user input of the plurality of user inputs from only one of the first user interface and the second user interface, (I) determining from the plurality of operations, based on the first user input and the next user input, a first operation thereof and a next operation thereof that are associated, respectively, with the first user input and the next user input, and controlling, according to the determination of the first operation and the next operation, the first user interface and the second user interface to display information associated with the first operation, the next operation, and a current operational state of the power injector system; and (b) upon receiving the first user input of the plurality of user inputs and the next user input of the plurality of user inputs from one of the first user interface and the second user interface and the other of the first user interface and the second user interface, respectively, and further: (I) upon determining that the first operation and the next operation associated, respectively, with the first user input and the next user input are of a type that can be performed independently, controlling, according to the determination, (i) the first user interface and the second user interface to display the information associated with the first operation, the next operation, and the current operational state of the power injector system and (ii) the first user interface and the second user interface to cooperatively accept current user input associated with the current operational state of the power injector system; and (II) upon determining that the first operation and the next operation associated, respectively, with the first user input and the next user input are of a type that can be performed only sequentially, controlling, according to the determination, the first user interface and the second user interface to synchronize display of, but not mirror, the information associated with the first operation, the next operation, and the current operational state of the power injector system.

In some non-limiting embodiments or aspects, the instructions further cause the at least one processor to: control the first user interface to display the information associated with the first operation, the next operation, and the current operational state of the power injector system in a first visual layout; and control the second user interface to display the information associated with the first operation, the next operation, and the current operational state of the power injector system in a second visual layout different than the first visual layout.

In some non-limiting embodiments or aspects, the instructions further cause the at least one processor to: control a third user interface of the power injector system, wherein the third user interface is configured to accept the plurality of user inputs associated with control of the plurality of operations of the power injector system, and wherein the third user interface is configured to display information associated with the plurality of operations of the power injector system.

In some non-limiting embodiments or aspects, the instructions further cause the at least one processor to: control the one of the first user interface and the second user interface and the other of the first user interface and the second user interface to simultaneously accept the first user input of the plurality of user inputs and the next user input of the plurality of user inputs, respectively.

In some non-limiting embodiments or aspects, the first user input and the next user input are associated with a same operational state of the power injector system.

In some non-limiting embodiments or aspects, the first user input and the next user input are associated with different operational states of the power injector system.

In some non-limiting embodiments or aspects, the instructions further cause the at least one processor to: control the one of the first user interface and the second user interface and the other of the first user interface and the second user interface to prevent acceptance of the next user input and the first user input, respectively.

In some non-limiting embodiments or aspects, the current operational state of the power injector system is different than the first operation and the next operation.

In some non-limiting embodiments or aspects, the instructions further cause the at least one processor to: control the second user interface to provide a prompt that requests a user to input the next user input via the first user interface.

According to some non-limiting embodiments or aspects, provided is a computer-implemented method for controlling a first user interface and a second user interface of a power injector system having a power injector for enabling delivery of fluid in an injection procedure to be performed on a patient, the first user interface and the second user interface being configured to accept a plurality of user inputs associated with control of a plurality of operations of the power injector system and display information associated with the plurality of operations of the power injector system, and one of the first user interface and the second user interface being proximate to the power injector and the other of the first user interface and the second user interface being remote from the power injector, the method comprising: (a) upon receiving a first user input of the plurality of user inputs and a next user input of the plurality of user inputs from only one of the first user interface and the second user interface, (I) determining, with at least one processor, from the plurality of operations, based on the first user input and the next user input, a first operation thereof and a next operation thereof that are associated, respectively, with the first user input and the next user input, and controlling, with at least one processor, according to the determination of the first operation and the next operation, the first user interface and the second user interface to display information associated with the first operation, the next operation, and a current operational state of the power injector system; and (b) upon receiving the first user input of the plurality of user inputs and the next user input of the plurality of user inputs from one of the first user interface and the second user interface and the other of the first user interface and the second user interface, respectively, and further: (I) upon determining that the first operation and the next operation associated, respectively, with the first user input and the next user input are of a type that can be performed independently, controlling, with at least one processor, according to the determination, (i) the first user interface and the second user interface to display the information associated with the first operation, the next operation, and the current operational state of the power injector system and (ii) the first user interface and the second user interface to cooperatively accept current user input associated with the current operational state of the power injector system; and (II) upon determining that the first operation and the next operation associated, respectively, with the first user input and the next user input are of a type that can be performed only sequentially, controlling, with at least one processor, according to the determination, the first user interface and the second user interface to synchronize display of, but not mirror, the information associated with the first operation, the next operation, and the current operational state of the power injector system.

According to some non-limiting embodiments or aspects, provided is a method for providing independent user interfaces for operating a power injector system, wherein the power injector system includes a first user interface, a second user interface, and a power injector for delivering fluid to a patient, the method including: receiving, via the first user interface with a computer system including one or more processors, a first user input; determining, with the computer system, a first operation of the power injector system that is associated with the first user interface based on the first user input; and controlling, with the computer system, the second user interface based on the first operation associated with the first user interface, wherein one of the first user interface and the second user interface is proximate the power injector, and wherein the other of the first user interface and the second user interface is remote from the power injector.

In some non-limiting embodiments or aspects, the first user interface includes a first graphical user interface, wherein the second user interface includes a second graphical user interface, the method further including: controlling, with the computer system, the first graphical user interface to display information associated with the first user input in a first visual layout; and controlling, with the computer system, the second graphical user interface to display the information associated with the first user input in a second visual layout different than the first visual layout.

In some non-limiting embodiments or aspects, controlling the second user interface includes controlling the second user interface based on a location of the second user interface with respect to the power injector.

In some non-limiting embodiments or aspects, the method further includes receiving, via the second user interface with the computer system, a second user input simultaneously with receiving the first user input via the first user interface.

In some non-limiting embodiments or aspects, the first user input and the second user input are associated with a same operation of the power injector system.

In some non-limiting embodiments or aspects, the first user input is associated with the first operation of the power injector system, and wherein the second user input is associated with a second operation of the power injector system different than the first operation of the power injector system.

In some non-limiting embodiments or aspects, the method further includes controlling, with the computer system, the first user interface based on information associated with a first patient, wherein controlling the second user interface includes simultaneously controlling the second user interface based on information associated with a second patient different than the first patient and/or based on other non-patient associated tasks.

In some non-limiting embodiments or aspects, controlling the second user interface includes controlling the second user interface to prevent input of second user input via the second user interface.

In some non-limiting embodiments or aspects, the method further includes receiving, via the second user interface with the computer system, a third user input, wherein the third user input is associated with a different operation of the power injector system than the next user input.

In some non-limiting embodiments or aspects, controlling the second user interface includes controlling the second user interface to provide a prompt that requests a user to input a second user input via the first user interface.

According to some non-limiting embodiments or aspects, provided is a power injector system including: a power injector configured to deliver fluid to a patient; a first user interface; a second user interface; and a computer system including one or more processors, wherein the computer system is programmed or configured to: receive, via the first user interface, a first user input; determine a first operation of the power injector system that is associated with the first user interface based on the first user input; and control the second user interface based on the first operation associated with the first user interface, wherein one of the first user interface and the second user interface is proximate the power injector, and wherein the other of the first user interface and the second user interface is remote from the power injector.

In some non-limiting embodiments or aspects, the first user interface includes a first graphical user interface, wherein the second user interface includes a second graphical user interface, and wherein the computer system is further programmed or configured to: control the first graphical user interface to display information associated with the first user input in a first visual layout; and control the second graphical user interface to display the information associated with the first user input in a second visual layout different than the first visual layout.

In some non-limiting embodiments or aspects, the computer system is further programmed or configured to control the second user interface based on a location of the second user interface with respect to the power injector.

In some non-limiting embodiments or aspects, the computer system is further programmed or configured to receive a second user input simultaneously with receiving the first user input via the first user interface.

In some non-limiting embodiments or aspects, the first user input and the second user input are associated with a same operation of the power injector system.

In some non-limiting embodiments or aspects, the first user input is associated with the first operation of the power injector system, and the second user input is associated with a second operation of the power injector system different than the first operation of the power injector system.

In some non-limiting embodiments or aspects, the computer system is further programmed or configured to control the first user interface based on information associated with a first patient; and simultaneously control the second user interface based on information associated with a second patient different than the first patient.

In some non-limiting embodiments or aspects, the computer system is further programmed or configured to control the second user interface to prevent input of a second user input via the second user interface.

In some non-limiting embodiments or aspects, the computer system is further programmed or configured to receive, via the second user interface, a third user input, wherein the third user input is associated with a different operation of the power injector system than the second user input.

In some non-limiting embodiments or aspects, the computer system is further programmed or configured to control the second user interface to provide a prompt that requests a user to input a second user input via the first user interface.

Further non-limiting embodiments or aspects are set forth in the following numbered clauses:

Clause 1. A power injector system having a power injector for enabling delivery of fluid in an injection procedure to be performed on a patient, the power injector system comprising: one or more processors; a first user interface; and a second user interface, wherein the first user interface and the second user interface are configured to accept a plurality of user inputs associated with control of a plurality of operations of the power injector system, wherein the first user interface and the second user interface are configured to display information associated with the plurality of operations of the power injector system, wherein one of the first user interface and the second user interface is proximate to the power injector and the other of the first user interface and the second user interface is remote from the power injector, wherein the one or more processors are programmed and/or configured to: (a) upon receiving a first user input of the plurality of user inputs and a next user input of the plurality of user inputs from only one of the first user interface and the second user interface, (I) determine from the plurality of operations, based on the first user input and the next user input, a first operation thereof and a next operation thereof that are associated, respectively, with the first user input and the next user input, and control, according to the determination of the first operation and the next operation, the first user interface and the second user interface to display information associated with the first operation, the next operation, and a current operational state of the power injector system; and (b) upon receiving the first user input of the plurality of user inputs and the next user input of the plurality of user inputs from one of the first user interface and the second user interface and the other of the first user interface and the second user interface, respectively, and further: (I) upon determining that the first operation and the next operation associated, respectively, with the first user input and the next user input are of a type that can be performed independently, control, according to the determination, (i) the first user interface and the second user interface to display the information associated with the first operation, the next operation, and the current operational state of the power injector system and (ii) the first user interface and the second user interface to cooperatively accept current user input associated with the current operational state of the power injector system; and (II) upon determining that the first operation and the next operation associated, respectively, with the first user input and the next user input are of a type that can be performed only sequentially, control, according to the determination, the first user interface and the second user interface to synchronize display of, but not mirror, the information associated with the first operation, the next operation, and the current operational state of the power injector system.

Clause 2. The system of clause 1, wherein the one or more processors are further programmed and/or configured to: control the first user interface to display the information associated with the first operation, the next operation, and the current operational state of the power injector system in a first visual layout; and control the second user interface to display the information associated with the first operation, the next operation, and the current operational state of the power injector system in a second visual layout different than the first visual layout.

Clause 3. The system of any of clauses 1 and 2, further comprising: a third user interface, wherein the third user interface is configured to accept the plurality of user inputs associated with control of the plurality of operations of the power injector system, and wherein the third user interface is configured to display information associated with the plurality of operations of the power injector system.

Clause 4. The system of any of clauses 1-3, wherein the one or more processors are further programmed and/or configured to: control the one of the first user interface and the second user interface and the other of the first user interface and the second user interface to simultaneously accept the first user input of the plurality of user inputs and the next user input of the plurality of user inputs, respectively.

Clause 5. The system of any of clauses 1-4, wherein the first user input and the next user input are associated with a same operational state of the power injector system.

Clause 6. The system of any of clauses 1-5, wherein the first user input and the next user input are associated with different operational states of the power injector system.

Clause 7. The system of any of clauses 1-6, wherein the one or more processors are further programmed and/or configured to: control the first user interface based on information associated with a first patient; and simultaneously control the second user interface based on information associated with a second patient different than the first patient.

Clause 8. The system of any of clauses 1-7, wherein the one or more processors are further programmed and/or configured to: control the one of the first user interface and the second user interface and the other of the first user interface and the second user interface to prevent acceptance of the next user input and the first user input, respectively.

Clause 9. The system of any of clauses 1-8, wherein the current operational state of the power injector system is different than the first operation and the next operation.

Clause 10. The system of any of clauses 1-9, wherein the one or more processors are further programmed and/or configured to: control the second user interface to provide a prompt that requests a user to input the next user input via the first user interface.

Clause 11. A computer program product comprising at least one non-transitory computer-readable medium including program instructions that, when executed by at least one processor, cause the at least one processor to: control a first user interface and a second user interface of a power injector system having a power injector for enabling delivery of fluid in an injection procedure to be performed on a patient, wherein the first user interface and the second user interface are configured to accept a plurality of user inputs associated with control of a plurality of operations of the power injector system, wherein the first user interface and the second user interface are configured to display information associated with the plurality of operations of the power injector system, wherein one of the first user interface and the second user interface is proximate to the power injector and the other of the first user interface and the second user interface is remote from the power injector, and wherein the instructions cause the at least one processor to control the first user interface and the second user interface by: (a) upon receiving a first user input of the plurality of user inputs and a next user input of the plurality of user inputs from only one of the first user interface and the second user interface, (I) determining from the plurality of operations, based on the first user input and the next user input, a first operation thereof and a next operation thereof that are associated, respectively, with the first user input and the next user input, and controlling, according to the determination of the first operation and the next operation, the first user interface and the second user interface to display information associated with the first operation, the next operation, and a current operational state of the power injector system; and (b) upon receiving the first user input of the plurality of user inputs and the next user input of the plurality of user inputs from one of the first user interface and the second user interface and the other of the first user interface and the second user interface, respectively, and further: (I) upon determining that the first operation and the next operation associated, respectively, with the first user input and the next user input are of a type that can be performed independently, controlling, according to the determination, (i) the first user interface and the second user interface to display the information associated with the first operation, the next operation, and the current operational state of the power injector system and (ii) the first user interface and the second user interface to cooperatively accept current user input associated with the current operational state of the power injector system; and (II) upon determining that the first operation and the next operation associated, respectively, with the first user input and the next user input are of a type that can be performed only sequentially, controlling, according to the determination, the first user interface and the second user interface to synchronize display of, but not mirror, the information associated with the first operation, the next operation, and the current operational state of the power injector system.

Clause 12. The computer program product of clause 11, wherein the instructions further cause the at least one processor to: control the first user interface to display the information associated with the first operation, the next operation, and the current operational state of the power injector system in a first visual layout; and control the second user interface to display the information associated with the first operation, the next operation, and the current operational state of the power injector system in a second visual layout different than the first visual layout.

Clause 13. The computer program product of any of clauses 11 and 12, wherein the instructions further cause the at least one processor to: control a third user interface of the power injector system, wherein the third user interface is configured to accept the plurality of user inputs associated with control of the plurality of operations of the power injector system, and wherein the third user interface is configured to display information associated with the plurality of operations of the power injector system.

Clause 14. The computer program product of any of clauses 11-13, wherein the instructions further cause the at least one processor to: control the one of the first user interface and the second user interface and the other of the first user interface and the second user interface to simultaneously accept the first user input of the plurality of user inputs and the next user input of the plurality of user inputs, respectively.

Clause 15. The computer program product of any of clauses 11-14, wherein the first user input and the next user input are associated with a same operational state of the power injector system.

Clause 16. The computer program product of any of clauses 11-15, wherein the first user input and the next user input are associated with different operational states of the power injector system.

Clause 17. The computer program product of any of clauses 11-16, wherein the instructions further cause the at least one processor to: control the one of the first user interface and the second user interface and the other of the first user interface and the second user interface to prevent acceptance of the next user input and the first user input, respectively.

Clause 18. The computer program product of any of clauses 11-17, wherein the current operational state of the power injector system is different than the first operation and the next operation.

Clause 19. The computer program product of any of clauses 11-18, wherein the instructions further cause the at least one processor to: control the second user interface to provide a prompt that requests a user to input the next user input via the first user interface.

Clause 20. A computer-implemented method for controlling a first user interface and a second user interface of a power injector system having a power injector for enabling delivery of fluid in an injection procedure to be performed on a patient, the first user interface and the second user interface being configured to accept a plurality of user inputs associated with control of a plurality of operations of the power injector system and display information associated with the plurality of operations of the power injector system, and one of the first user interface and the second user interface being proximate to the power injector and the other of the first user interface and the second user interface being remote from the power injector, the method comprising: (a) upon receiving a first user input of the plurality of user inputs and a next user input of the plurality of user inputs from only one of the first user interface and the second user interface, (I) determining, with at least one processor, from the plurality of operations, based on the first user input and the next user input, a first operation thereof and a next operation thereof that are associated, respectively, with the first user input and the next user input, and controlling, with at least one processor, according to the determination of the first operation and the next operation, the first user interface and the second user interface to display information associated with the first operation, the next operation, and a current operational state of the power injector system; and (b) upon receiving the first user input of the plurality of user inputs and the next user input of the plurality of user inputs from one of the first user interface and the second user interface and the other of the first user interface and the second user interface, respectively, and further: (I) upon determining that the first operation and the next operation associated, respectively, with the first user input and the next user input are of a type that can be performed independently, controlling, with at least one processor, according to the determination, (i) the first user interface and the second user interface to display the information associated with the first operation, the next operation, and the current operational state of the power injector system and (ii) the first user interface and the second user interface to cooperatively accept current user input associated with the current operational state of the power injector system; and (II) upon determining that the first operation and the next operation associated, respectively, with the first user input and the next user input are of a type that can be performed only sequentially, controlling, with at least one processor, according to the determination, the first user interface and the second user interface to synchronize display of, but not mirror, the information associated with the first operation, the next operation, and the current operational state of the power injector system.

Clause 21. A method for providing independent user interfaces for operating a power injector system, wherein the power injector system comprises a first user interface, a second user interface, and a power injector for delivering fluid to a patient, the method comprising: receiving, via the first user interface with a computer system comprising one or more processors, a first user input; determining, with the computer system, a first operation of the power injector system that is associated with the first user interface based on the first user input; and controlling, with the computer system, the second user interface based on the first operation associated with the first user interface, wherein one of the first user interface and the second user interface is proximate the power injector, and wherein the other of the first user interface and the second user interface is remote from the power injector.

Clause 22. The method of clause 21, wherein the first user interface includes a first graphical user interface, wherein the second user interface includes a second graphical user interface, the method further comprising: controlling, with the computer system, the first graphical user interface to display information associated with the first user input in a first visual layout; and controlling, with the computer system, the second graphical user interface to display the information associated with the first user input in a second visual layout different than the first visual layout.

Clause 23. The method of any of clauses 21 and 22, wherein controlling the second user interface includes controlling the second user interface based on a location of the second user interface with respect to the power injector.

Clause 24. The method of any of clauses 21-23, further comprising: receiving, via the second user interface with the computer system, a second user input simultaneously with receiving the first user input via the first user interface.

Clause 25. The method of any of clauses 21-24, wherein the first user input and the second user input are associated with a same operation of the power injector system.

Clause 26. The method of any of clause 21-25, wherein the first user input is associated with the first operation of the power injector system, and wherein the second user input is associated with a second operation of the power injector system different than the first operation of the power injector system.

Clause 27. The method of any of clauses 21-26, further comprising: controlling, with the computer system, the first user interface based on information associated with a first patient, wherein controlling the second user interface includes simultaneously controlling the second user interface based on information associated with a second patient different than the first patient and/or based on other non-patient associated tasks.

Clause 28. The method of any of clauses 21-27, wherein controlling the second user interface includes controlling the second user interface to prevent input of second user input via the second user interface.

Clause 29. The method of any of clauses 21-28, further comprising: receiving, via the second user interface with the computer system, a third user input, wherein the third user input is associated with a different operation of the power injector system than the second user input.

Clause 30. The method of any of clauses 21-29, wherein controlling the second user interface includes controlling the second user interface to provide a prompt that requests a user to input second user input via the first user interface.

Clause 31. A power injector system comprising: a power injector configured to deliver fluid to a patient; a first user interface; a second user interface; and a computer system comprising one or more processors, wherein the computer system is programmed or configured to: receive, via the first user interface, a first user input; determine a first operation of the power injector system that is associated with the first user interface based on the first user input; and control the second user interface based on the first operation associated with the first user interface, wherein one of the first user interface and the second user interface is proximate the power injector, and wherein the other of the first user interface and the second user interface is remote from the power injector.

Clause 32. The system of clause 31, wherein the first user interface includes a first graphical user interface, wherein the second user interface includes a second graphical user interface, and wherein the computer system is further programmed or configured to: control the first graphical user interface to display information associated with the first user input in a first visual layout; and control the second graphical user interface to display the information associated with the first user input in a second visual layout different than the first visual layout.

Clause 33. The system of any of clauses 31 and 32, wherein the computer system is further programmed or configured to: control the second user interface based on a location of the second user interface with respect to the power injector.

Clause 34. The system of any of clauses 31-33, wherein the computer system is further programmed or configured to: receive a second user input simultaneously with receiving the first user input via the first user interface.

Clause 35. The system of any of clauses 31-34, wherein the first user input and the second user input are associated with a same operation of the power injector system.

Clause 36. The system of any of clauses 31-35, wherein the first user input is associated with the first operation of the power injector system, and wherein the second user input is associated with a second operation of the power injector system different than the first operation of the power injector system.

Clause 37. The system of any of clauses 31-36, wherein the computer system is further programmed or configured to: control the first user interface based on information associated with a first patient; and simultaneously control the second user interface based on information associated with a second patient different than the first patient and/or based on other non-patient associated tasks.

Clause 38. The system of any of clauses 31-37, wherein the computer system is further programmed or configured to: control the second user interface to prevent input of second user input via the second user interface.

Clause 39. The system of any of clauses 31-38 wherein the computer system is further programmed or configured to: receive, via the second user interface, third user input, wherein the third user input is associated with a different operation of the power injector system than the second user input.

Clause 40. The system of any of clauses 31-39, wherein the computer system is further programmed or configured to: control the second user interface to provide a prompt that requests a user to input second user input via the first user interface.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

BRIEF DESCRIPTION OF THE DRAWINGS

Additional advantages and details are explained in greater detail below with reference to the exemplary embodiments that are illustrated in the accompanying schematic figures and appendices, in which.

DESCRIPTION

Figure 1:
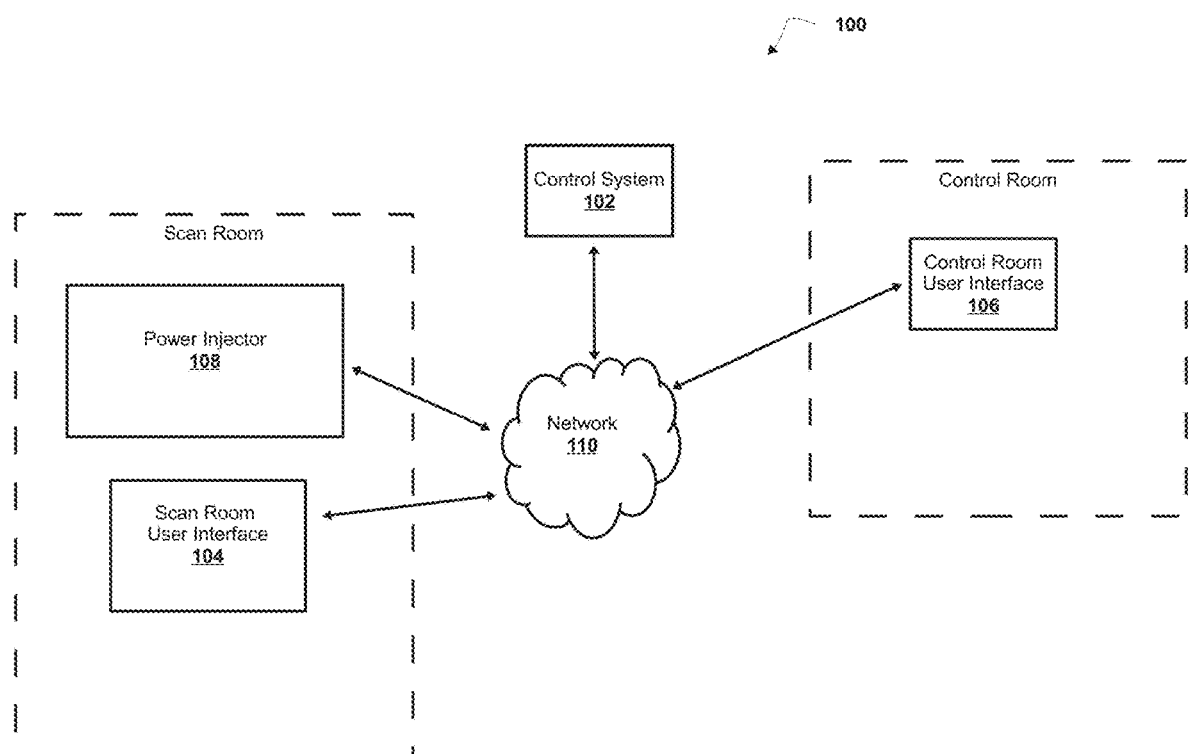
FIG. 1 is a diagram of non-limiting embodiments or aspects of an environment in which systems, devices, products, apparatuses, and/or methods, described herein, can be implemented.

It is to be understood that the present disclosure may assume various alternative variations and step sequences, except where expressly specified to the contrary. It is also to be understood that the specific devices and processes illustrated in the attached drawings and described in the following specification are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible.

As used herein, the term "computing device" may refer to one or more electronic devices that are configured to directly or indirectly communicate with or over one or more networks. A computing device may be a mobile or portable computing device, a desktop computer, a server, and/or the like. Furthermore, the term "computer" may refer to any computing device that includes the necessary components to receive, process, and output data, and normally includes a display, a processor, a memory, an input device, and a network interface. A "computing system" may include one or more computing devices or computers. An "application" or "application program interface" (API) refers to computer code or other data stored on a computer-readable medium that may be executed by a processor to facilitate the interaction between software components, such as a client-side front-end and/or a server-side back-end for receiving data from the client. An "interface" refers to a generated display, such as one or more graphical user interfaces (GUIs) with which a user may interact, either directly or indirectly (e.g., through a keyboard, a mouse, a touchscreen, etc.). Further, multiple computers, e.g., servers, or other computerized devices, directly or indirectly communicating in the network environment may constitute a "system" or a "computing system".

It will be apparent that the systems, computer program products and/or methods described herein, can be implemented in different forms of hardware, software, or a combination of hardware and software. The actual specialized control hardware or software code used to implement these systems, computer program products and/or methods is not limiting of the implementations. Thus, the operation and behavior of the systems, computer program products and/or methods are described herein without reference to specific software code, it being understood that software and hardware can be designed to implement the systems, computer program products and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Provided are improved systems, devices, products, apparatuses, and/or methods for power injector system operation.

An existing power injector system includes a power injector (e.g., an injection mechanism) in a scan room with a patient (e.g., a scan room unit) and an operator display or console in a control room for setup and monitoring of an injection procedure (e.g., a control room unit). For example, the scan room unit and the control room unit may share a set of common tasks, functionalities, or operations that can be performed at either location (e.g., patient/procedure setup, injection protocol setup, exam execution and injection monitoring, etc.), and each of the scan room unit and the control room unit may have unique tasks, functionalities, or operations that may be performed only at that location (e.g., fluid loading and delivery at the scan room unit, protocol management at the control room unit, etc.). As an example, sequential operations at each location may be performed by a single user, sequential and/or simultaneous operations at each location may be performed by two separate users, some operations or user interface displays may only be available at one of the locations and/or only under certain circumstances, and/or some operations may only be partially performed at one location and a remainder of the operations performed (e.g., performed, completed, etc.) at the other location.

However, an existing power injector system may have a constrained or limited user interface in the scan room in order to more easily maintain shared system state and enable multiple users in multiple locations to interact with the power injector system without conflict. For example, using multiple separated points of user interaction increases the difficultly of maintaining coordination of the operational state of the power injector system between the multiple locations, which is further increased when more than one user interacts with the power injector system from each location (e.g., either sequentially or simultaneously). As an example, some existing power injector systems have a reduced functionality user interface in the scan room, such as a reduced display (e.g., a pre-segmented display associated with predefined operation, a text only display, etc.) and/or physical buttons programmed or configured for more basic operations, which means that scan room functionality can be overly limited and more user interaction with system software occurs on a graphical user interface (GUI) in the control room. As an example, some existing power injector systems use a screen mirroring approach where a GUI in each location is an exact copy of the other location and user interaction with each GUI is location independent, which means that location specific operations cannot be implemented and that only one operation at a time can be performed.

In this way, existing power injector systems may not support independent operation of multiple user interfaces by multiple users in a sequential and/or simultaneous manner. Accordingly, contrast delivery procedures may be less efficient and/or more time consuming, multiple users may be required to be more aware of each other's activities to avoid conflicts between operations at different user interface locations, and/or single users may be required to travel more often between user interface locations (i.e., between the scan and control rooms) to perform certain operations and/or ensure correct operation of the power injector system.

Non-limiting embodiments or aspects of the present disclosure are directed to systems, devices, products, apparatus, and/or methods for independent user interfaces for power injector system operation. A power injector system having a power injector for enabling delivery of fluid in an injection procedure to be performed on a patient may include one or more processors; a first user interface; and a second user interface. The first user interface and the second user interface may be configured to accept a plurality of user inputs associated with control of a plurality of operations of the power injector system. The first user interface and the second user interface may be configured to display information associated with the plurality of operations of the power injector system. One of the first user interface and the second user interface may be proximate to the power injector (e.g., in a scan room, etc.) and the other of the first user interface and the second user interface may be remote from the power injector (e.g., in a control room, etc.). The one or more processors may be programmed and/or configured to: (a) upon receiving a first user input of the plurality of user inputs and a next user input of the plurality of user inputs from only one of the first user interface and the second user interface, (I) determine from the plurality of operations, based on the first user input and the next user input, a first operation thereof and a next operation thereof that are associated, respectively, with the first user input and the next user input, and control, according to the determination of the first operation and the next operation, the first user interface and the second user interface to display information associated with the first operation, the next operation, and a current operational state of the power injector system; and (b) upon receiving the first user input of the plurality of user inputs and the next user input of the plurality of user inputs from one of the first user interface and the second user interface and the other of the first user interface and the second user interface, respectively, and further: (I) upon determining that the first operation and the next operation associated, respectively, with the first user input and the next user input are of a type that can be performed independently, control, according to the determination, (i) the first user interface and the second user interface to display the information associated with the first operation, the next operation, and the current operational state of the power injector system and (ii) the first user interface and the second user interface to cooperatively accept current user input associated with the current operational state of the power injector system; and (II) upon determining that the first operation and the next operation associated, respectively, with the first user input and the next user input are of a type that can be performed only sequentially, control, according to the determination, the first user interface and the second user interface to synchronize display of, but not mirror, the information associated with the first operation, the next operation, and the current operational state of the power injector system.

In this way, a power injector system can provide independent operation of multiple user interfaces by multiple users in a sequential and/or simultaneous manner. Accordingly, contrast delivery procedures may be more efficient and/or less time consuming, multiple users can be less aware of each other's activities, conflicts between operations at different user interface locations may be more easily and efficiently avoided without overly limiting user interface functionality, and/or single users may be required to travel less often between user interface locations to perform certain operations and/or ensure correct power injector system operation.

Referring now to FIG. 1, FIG. 1 is a diagram of non-limiting embodiments or aspects of an environment in which systems, devices, products, apparatuses, and/or methods, described herein, can be implemented. As shown in FIG. 1, the environment includes power injector system 100. Power injector system 100 includes control system 102, scan room user interface 104, control room user interface 106, power injector 108, and network 110. Systems and/or devices of power injector system 100 shown in FIG. 1 can interconnect via wired connections, wireless connections, or a combination of wired and wireless connections. For example, systems and/or devices of power injector system 100 may interconnect and/or communicate information and/or data via network 110.

In some non-limiting embodiments or aspects, power injector system 100 includes a total or integrated system for generating, dose preparation, and administration of radiopharmaceutical agents as described in U.S. application Ser. No. 15/129,024, filed on Apr. 3, 2015, published as U.S. Patent Application Publication No. 2017/0172527, and assigned to the assignee of the present disclosure, the contents of which is hereby incorporated by reference in its entirety.

In some non-limiting embodiments or aspects, control system 102 includes one or more devices capable of receiving, via a first user interface (e.g., scan room user interface 104, control room user interface 106, etc.), a first user input, determining a first operation of power injector system 100 (e.g., an operation associated with one or more systems or devices of power injector system 100) that is associated with the first user interface based on the first user input, and controlling the second user interface (e.g., scan room user interface 104, control room user interface 106, etc.) based on the first operation associated with the first user interface. For example, control system 102 can include one or more computing systems including one or more processors (e.g., one or more servers, etc.). In some non-limiting embodiments or aspects, for example, as shown in FIG. 1, control system 102 is separate and/or remote from scan room user interface 104, control room user interface 106, and power injector 108. In some non-limiting embodiments or aspects, control system 102 can be implemented within or distributed across one or more of scan room user interface 104, control room user interface 106, and power injector 108.

In some non-limiting embodiments or aspects, scan room user interface 104 includes one or more devices capable of providing output to a user and receiving user input from a user. For example, scan room user interface 104 can include one or more input components that permit scan room user interface 104 to receive information via user input (e.g., a touch screen display, a keyboard, a keypad, a mouse, a button, a switch, a microphone, etc.), and one or more output components that provide output information (e.g., a display, a speaker, one or more light-emitting diodes (LEDs), etc.). In some non-limiting embodiments or aspects, scan room user interface 104 includes a graphical user interface (GUI). For example, scan room user interface 104 includes a GUI configured to display relevant data obtained by power injector system 100 and to receive control data and parameters to operate power injector system 100. In some non-limiting embodiments or aspects, scan room user interface 104 includes a GUI as described in U.S. application Ser. No. 15/129,024, filed on Apr. 3, 2015, published as U.S. Patent Application Publication No. 2017/0172527, and assigned to the assignee of the present disclosure, the contents of which is hereby incorporated by reference in its entirety. In some non-limiting embodiments or aspects, scan room user interface 104 is located proximate to power injector 108. For example, scan room user interface 104 can be located in a scan room with power injector 108 and a patient. As an example, scan room user interface 104 can be positioned adjacent to power injector 108, mechanically and/or electrically connected (e.g., directly connected) to power injector 108, implemented within power injector 108, and/or the like.

In some non-limiting embodiments or aspects, control room user interface 106 includes one or more devices capable of providing output to a user and receiving user input from a user. For example, control room user interface 106 can include one or more input components that permit control room user interface 106 to receive information via user input (e.g., a touch screen display, a keyboard, a keypad, a mouse, a button, a switch, a microphone, etc.), and one or more output components that provide output information (e.g., a display, a speaker, one or more light-emitting diodes (LEDs), etc.). In some non-limiting embodiments or aspects, control room user interface 106 includes a graphical user interface (GUI). For example, control room user interface 106 includes a GUI configured to display relevant data obtained by power injector system 100 and to receive control data and parameters to operate power injector system 100. In some non-limiting embodiments or aspects, control room user interface 106 includes a GUI as described in U.S. application Ser. No. 15/129,024, filed on Apr. 3, 2015, published as U.S. Patent Application Publication No. 2017/0172527, and assigned to the assignee of the present disclosure, the contents of which is hereby incorporated by reference in its entirety. In some non-limiting embodiments or aspects, control room user interface 106 is located remote from power injector 108 and/or scan room user interface 104. For example, control room user interface 106 can be located in a control room. As an example, control room user interface 106 can be positioned in a shielded control room outside the scan room that enables a user to monitor power injector system 100 in a safe and convenient location.

In some non-limiting embodiments or aspects, power injector 108 includes one or more devices capable of delivering fluid to a patient. For example, power injector 108 can include the MEDRAD® Centargo CT Injection System, the MEDRAD® Stellant CT Injection System, the MEDRAD® Mark 7 Arterion Injection System, the MEDRAD® Avanta Fluid Management Injection System, the MEDRAD® MRXperion MR Injection System, and/or the like, each of which is offered by Bayer HealthCare LLC. Power injector 108 may also include the Ulrich Medical CT Motion™ Injector, the Bracco Diagnostic, Inc. CT Exprès® Injector, and/or the injector disclosed in U.S. application Ser. No. 10/818,477, filed on Apr. 5, 2004, published as U.S. Patent Application Publication No. 2004/0254533, and assigned to the assignee of the present disclosure, the contents of which is hereby incorporated by reference in its entirety.

In some non-limiting embodiments or aspects, network 110 includes one or more wired and/or wireless networks. For example, network 110 includes a cellular network (e.g., a long-term evolution (LTE) network, a third generation (3G) network, a fourth generation (4G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of these or other types of networks.

The number and arrangement of systems, devices, and networks shown in FIG. 1 are provided as an example. There can be additional systems, devices, and/or networks, fewer systems, devices, and/or networks, different systems, devices, and/or networks, or differently arranged systems, devices, and/or networks than those shown in FIG. 1. Furthermore, two or more systems or devices shown in FIG. 1 can be implemented within a single system or a single device, or a single system or a single device shown in FIG. 1 can be implemented as multiple, distributed systems or devices. Additionally, or alternatively, a set of systems or a set of devices (e.g., one or more systems, one or more devices) of power injector system 100 can perform one or more functions described as being performed by another set of systems or another set of devices of power injector system 100.

Figure 2:
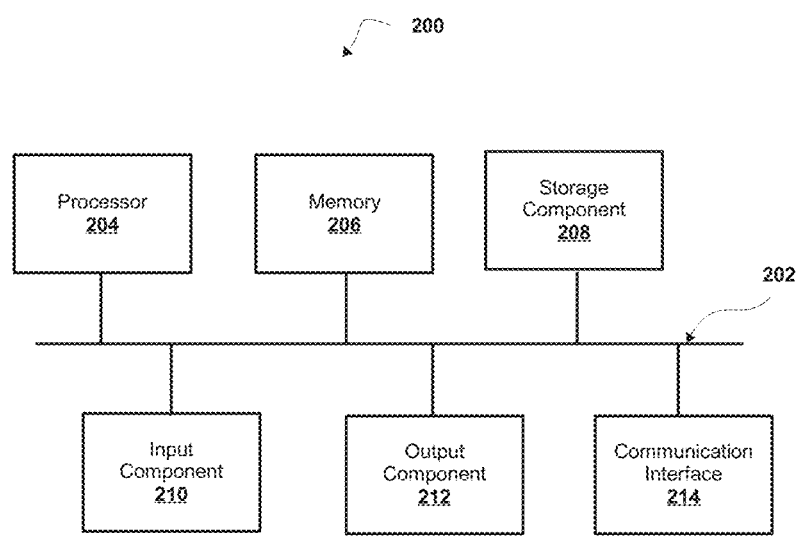
FIG. 2 is a diagram of non-limiting embodiments or aspects of components of one or more devices, one or more systems, and/or one or more interfaces of FIG. 1.

Referring now to FIG. 2, FIG. 2 is a diagram of example components of a device 200. Device 200 can correspond to one or more devices of control system 102, one or more devices of (e.g., one or more devices of a system of) scan room user interface 104, one or more devices of (e.g., one or more devices of a system of) control room user interface 106, and/or one or more devices of (e.g., one or more devices of a system of) power injector 108. In some non-limiting embodiments or aspects, one or more devices of control system 102, one or more devices of (e.g., one or more devices of a system of) scan room user interface 104, one or more devices of (e.g., one or more devices of a system of) control room user interface 106, and/or one or more devices of (e.g., one or more devices of a system of) power injector 108 can include at least one device 200 and/or at least one component of device 200. As shown in FIG. 2, device 200 includes bus 202, processor 204, memory 206, storage component 208, input component 210, output component 212, and communication interface 214.

Bus 202 includes a component that permits communication among the components of device 200. In some non-limiting embodiments or aspects, processor 204 is implemented in hardware, firmware, or a combination of hardware and software. For example, processor 204 includes a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 includes a random access memory (RAM), a read only memory (ROM), and/or another type of dynamic or static storage device (e.g., flash memory, magnetic memory, optical memory, etc.) that stores information and/or instructions for use by processor 204.

Storage component 208 stores information and/or software related to the operation and use of device 200. For example, storage component 208 includes a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 includes a component that permits device 200 to receive information, such as via user input (e.g., a touch screen display, a keyboard, a keypad, a mouse, a button, a switch, a microphone, etc.). Additionally, or alternatively, input component 210 includes a sensor for sensing information (e.g., a global positioning system (GPS) component, an accelerometer, a gyroscope, an actuator, etc.). Output component 212 includes a component that provides output information from device 200 (e.g., a display, a speaker, one or more light-emitting diodes (LEDs), etc.).

Communication interface 214 includes a transceiver-like component (e.g., a transceiver, a separate receiver and transmitter, etc.) that enables device 200 to communicate with other devices, such as via a wired connection, a wireless connection, or a combination of wired and wireless connections. Communication interface 214 can permit device 200 to receive information from another device and/or provide information to another device. For example, communication interface 214 includes an Ethernet interface, an optical interface, a coaxial interface, an infrared interface, a radio frequency (RF) interface, a universal serial bus (USB) interface, a Wi-Fi interface, a cellular network interface, and/or the like.

Device 200 can perform one or more processes described herein. Device 200 can perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions can be read into memory 206 and/or storage component 208 from another computer-readable medium or from another device via communication interface 214. When executed, software instructions stored in memory 206 and/or storage component 208 cause processor 204 to perform one or more processes described herein. Additionally, or alternatively, hardwired circuitry can be used in place of or in combination with software instructions to perform one or more processes described herein. Thus, embodiments described herein are not limited to any specific combination of hardware circuitry and software.

The number and arrangement of components shown in FIG. 2 are provided as an example. In some non-limiting embodiments or aspects, device 200 includes additional components, fewer components, different components, or differently arranged components than those shown in FIG. 2. Additionally, or alternatively, a set of components (e.g., one or more components) of device 200 can perform one or more functions described as being performed by another set of components of device 200.

Figure 3A:
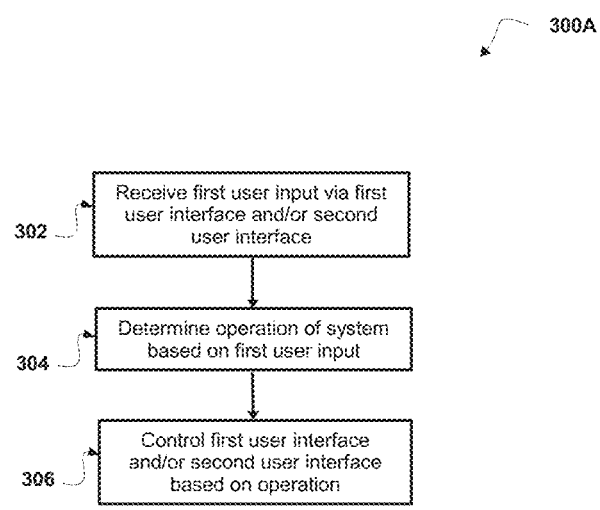
FIG. 3A is a flowchart of non-limiting embodiments or aspects of a process for providing independent user interfaces for operating a power injector system.

Referring now to FIG. 3A, FIG. 3A is a flowchart of non-limiting embodiments or aspects of a process 300A for providing independent user interfaces for operating a power injector system. In some non-limiting embodiments or aspects, one or more of the steps of process 300A are performed (e.g., completely, partially, etc.) by control system 102 (e.g., one or more devices of control system 102). In some non-limiting embodiments or aspects, one or more of the steps of process 300A are performed (e.g., completely, partially, etc.) by another device or a group of devices separate from or including control system 102, such as scan room user interface 104 (e.g., one or more devices of scan room user interface 104), control room user interface 106 (e.g., one or more devices of control room user interface 106), power injector 108 (e.g., one or more devices of power injector 108), and/or the like.

As shown in FIG. 3A, at step 302, process 300A includes receiving, via a first user interface and/or a second user interface, a first user input. For example, control system 102 receives the first user input via a first user interface and/or via a second user interface (e.g., user input received via scan room user interface 104, user input received via control room user interface 106, etc.). As an example, control system 102 controls a user interface (e.g., a GUI, etc.) to output text, graphical icons, visual indicators, and/or the like, and a user interacts with the user interface by inputting text and/or through manipulating the graphical icons, visual indicators, and/or the like. In such an example, the first user interface and the second user interface may be configured to accept a plurality of user inputs associated with control of a plurality of operations of power injector system 100, and the first user interface and the second user interface may be configured to provide (e.g., output, display, etc.) information associated with the plurality of operations of power injector system 100.

In some non-limiting embodiments or aspects, power injector system 100 may include at least one third user interface (not shown), which may be separated or remote from the first user interface and the second user interface (e.g., from scan room user interface 104 and control room user interface 106, etc.). For example, the third user interface may be configured to accept the plurality of user inputs associated with control of the plurality of operations of the power injector system, and the third user interface may be configured to display information associated with the plurality of operations of the power injector system.

In some non-limiting embodiments or aspects, user input is associated with a task, functionality, or operation of a workflow or process for operating power injector system 100. For example, a process for operating power injector system 100 (e.g., for configuring and performing an injection and/or imaging for a patient, etc.) can include a plurality of operations (e.g., power injector system 100 may operate in a plurality of operational states, etc.). As an example, a workflow for an injection and/or imaging procedure of power injector system 100 may include operations or operational states of power injector system 100 that receive and/or are associated with user input including one or more of the following: an identity of the patient (e.g., patient name, patient identification number, etc.), a preparation state or level of the patient (e.g., an indication of whether patient forms are completed, the patient is catheterized, the patient is pre-medicated, and/or the like), a procedure or protocol to be performed (e.g., an injection protocol to be used for the injection, a scan or imaging processing to be performed, etc.), parameters of the procedure or protocol (e.g., a time of an injection, a flow rate of contrast, a time of a scan or an imaging process, a type of contrast, etc.), an instruction to begin the procedure or protocol, analysis and/or notes on the injection and/or imaging procedure, and/or the like.

In some non-limiting embodiments or aspects, an operation of power injector system 100 can be associated with a first user interface and a second user interface. For example, an operation can be performed (e.g., user input associated with the operation can be received, output, such as a display, associated with the operation can be provided, etc.) at one or both of a first user interface and a second user interface (e.g., one or both of scan room user interface 104 and control room user interface 106, etc.). In some non-limiting embodiments or aspects, an operation of power injector system 100 can be associated with only a single user interface or location. For example, an operation can be performed (e.g., user input associated with the operation can be received, output, such as a display, associated with the operation can be provided, etc.) at only a first user interface or a second user interface.

In some non-limiting embodiments or aspects, an operation or operational state of power injector system 100 can include at least one of the following types of operations: a hardware and/or fluid loading type operation, an administrative and/or configuration type operation, an exam preparation and/or execution type operation, and/or the like. For example, a hardware and/or fluid loading type operation can be performed (e.g., control system 102 can receive user input associated with a hardware and/or fluid loading type operation, provide output, such as a display, associated with the hardware and/or fluid loading type operation, etc.) at scan room user interface 104 (e.g., partially at scan room user interface 104, primarily at scan room user interface 104, exclusively at scan room user interface 104, etc.), an administrative and/or configuration type operation can be performed (e.g., control system 102 can receive user input associated with an administrative and/or configuration type operation, provide output, such as a display, associated with the administrative and/or configuration type operation, etc.) at control room user interface (e.g., partially at control room user interface 106, primarily at control room user interface 106, exclusively at control room user interface 106, etc.), and/or an exam preparation and/or execution type operation can be performed (e.g., control system 102 can receive user input associated with an exam preparation and/or execution type operation, provide output, such as a display, associated with the exam preparation and/or execution type operation, etc.) at scan room user interface 104 and/or control room user interface 106 (e.g., partially at scan room user interface 104, primarily at scan room user interface 104, exclusively at scan room user interface 104, partially at control room user interface 106, primarily at control room user interface 106, exclusively at control room user interface 106, etc.).

In some non-limiting embodiments or aspects, an operation is associated with another operation in a sequential manner. For example, an operation may be performed sequentially (e.g., before or after, immediately before or after, etc.) in relation to another operation in a process for operating power injector system 100. For example, control system 102 can receive, via a user interface, user input associated with an operation before or after receiving user input associated with another operation that is scheduled to occur immediately before or after that operation in a process for operating power injector system 100. As an example, control system 102 can receive, via a first user interface, first user input associated with a first operation, and control the first user interface (and/or a second user interface) to perform another operation that is scheduled to occur immediately after the first operation based on the first user input.

In some non-limiting embodiments or aspects, an operation is associated with another operation in a parallel or simultaneous manner. For example, an operation of power injector system 100 is performed simultaneously as (e.g., in parallel with, at the same time as, etc.) another operation in a process for operating power injector system 100. For example, control system 102 receives via a first user interface, first user input associated with a first operation (and/or provides output, such as a display associated with the first operation via the first user interface) simultaneous to receiving, via a second user interface, second user input (e.g., a second user input, a next user input, etc.) associated with a second operation (and/or providing output, such as a display associated with the second operation via the second user interface). In some non-limiting embodiments or aspects, the first user input and the second user input are associated with a same operation. For example, control system 102 can receive, via a first user interface, a first user input associated with an operation at the same time as receiving, via a second user interface, a second user input associated with that same operation. In some non-limiting embodiments or aspects, the first user input is associated with a first operation, and the second user input is associated with a second operation different than the first operation.

In some non-limiting embodiments or aspects, simultaneously performed or parallel operations are independent from one another. For example, first user input associated with a first operation received via a first user interface may not modify a second operation that occurs simultaneously with the first operation. As an example, user input associated with a fluid loading operation that is received via scan room user interface 104 may be independent from a patient log editing operation that is being performed simultaneously via control room user interface 106. In some non-limiting embodiments or aspects, simultaneously performed or parallel operations interact with one another. For example, first user input associated with a first operation received via a first user interface may modify (e.g., modify, adjust, change, require updating, etc.) a second operation simultaneously that occurs simultaneously with the first operation. As an example, user input associated with an operation for editing an injection procedure or protocol received via control room interface 106 may interact with a fluid loading operation that is being performed simultaneously via scan room user interface 104.

As shown in FIG. 3A, at step 304, process 300A includes determining a first operation of a power injector system that is associated with a first user interface and/or a second user interface based on a first user input. For example, control system 102 determines a first operation of power injector system 100 (e.g., an operation associated with one or more systems or devices of power injector system 100) that is associated with the first user interface and/or the second user interface based on the first user input.

In some non-limiting embodiments or aspects, control system 102 determines an operation of power injector system 100 based on receiving user input associated with that operation, receiving user input associated with transitioning from another operation, and/or the like. For example, control system 102 can determine based on user input associated with an operation that a user interface of power injector system 100 (e.g., a user interface that received the user input, a user interface associated with an operation associated with the user input, etc.) is currently associated with (e.g., performing that operation, receiving user input associated with that operation, providing output, such as a display, associated with that operation, etc.) and/or determine based on user input associated with a transition from an operation to another operation (e.g., a transition between sequential operations, etc.) that a user interface of power injector system 100 (e.g., a user interface that received the user input, a user interface associated with an operation associated with the user input, etc.) is currently associated with (e.g., performing the another operation, receiving user input associated with the another operation, providing output, such as a display, associated with the another operation, etc.). As an example, control system 102 can determine that a first operation is currently associated with a first user interface based on user input associated with the first operation being received via the first user interface and/or based on user input associated with the first operation, which may be associated with the first user interface, being received via a second user interface. As an example, control system 102 can determine that a first operation is currently associated with a first user interface (and/or a second user interface) based on user input associated with transitioning from another operation that immediately proceeds the first operation being received via the first user interface and/or the second user interface in a process for operating power injector system 100.

As shown in FIG. 3A, at step 306, process 300A includes controlling a first user interface and/or a second user interface based on a first operation. For example, control system 102 may control a first user interface and/or a second user interface based on a first operation. As an example, control system 102 may control the first user interface and/or the second user interface (e.g., scan room user interface 104, control room user interface 106, etc.) based on the first operation. In such an example, control system 102 may control one of scan room user interface 104 and control room user interface 106 based on an operation currently associated with (e.g., performing that operation, receiving user input associated with that operation, providing output, such as a display, associated with that operation, etc.) the other of scan room user interface 104 and control room user interface 106.

In some non-limiting embodiments or aspects, the first user interface includes a first graphical user interface, and the second user interface includes a second graphical user interface. For example, control system 102 controls the first graphical user interface to display information associated with the first user input in a first visual layout, and controls the second graphical user interface to display the information associated with the first user input in a second visual layout different than the first visual layout. For example, control system 102 can independently control or drive the first user interface and the second user interface, but synchronize at least a portion of the first graphical user interface and the second graphical user interface, for example, by transitioning or snapping the second graphical user interface to provide the same or similar information as the first user interface, based on a first operation associated with the first user interface.

Further details regarding non-limiting embodiments or aspects of process 300A are provided below with regard to FIGS. 3B and 3C.

Figure 3B:
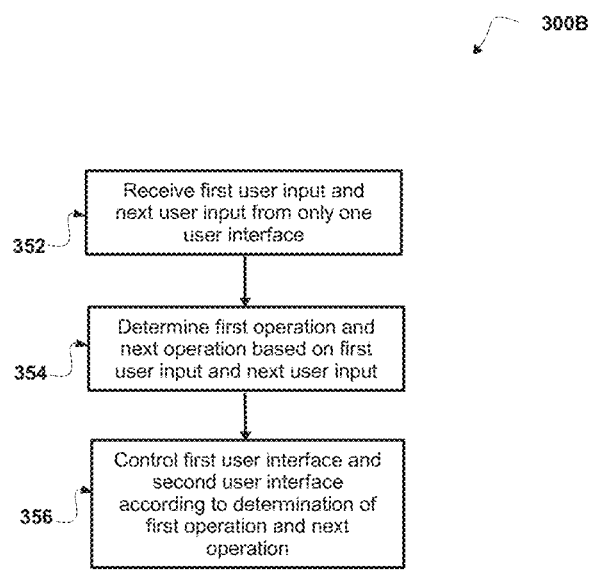
FIG. 3B is a flowchart of non-limiting embodiments or aspects of a process for providing independent user interfaces for operating a power injector system.

Referring now to FIG. 3B, FIG. 3B is a flowchart of non-limiting embodiments or aspects of a process 300B for providing independent user interfaces for operating a power injector system. In some non-limiting embodiments or aspects, one or more of the steps of process 300B are performed (e.g., completely, partially, etc.) by control system 102 (e.g., one or more devices of control system 102). In some non-limiting embodiments or aspects, one or more of the steps of process 300B are performed (e.g., completely, partially, etc.) by another device or a group of devices separate from or including control system 102, such as scan room user interface 104 (e.g., one or more devices of scan room user interface 104), control room user interface 106 (e.g., one or more devices of control room user interface 106), power injector 108 (e.g., one or more devices of power injector 108), and/or the like.

As shown in FIG. 3B, at step 352, process 300B includes receiving a first user input of the plurality of user inputs and a next user input of the plurality of user inputs from only one of the first user interface and the second user interface. For example, control system 102 may receive a first user input of the plurality of user inputs and a next user input of the plurality of user inputs from only one of the first user interface and the second user interface. As an example, a first user input of the plurality of user inputs and a next user input of the plurality of user inputs may be received via only one of the first user interface and the second user interface (e.g., only one of a scan room user interface and a control room user interface, etc.). In such an example, a user may include a single stationary user located at only one of the first user interface and the second user interface; however, it is noted that a passive viewer may be located at the other of the first user interface and the second user interface.

As shown in FIG. 3B, at step 354, process 300B includes, upon receiving a first user input of the plurality of user inputs and a next user input of the plurality of user inputs from only one of the first user interface and the second user interface, determining from the plurality of operations, based on the first user input and the next user input, a first operation thereof and a next operation thereof that are associated, respectively, with the first user input and the next user input. For example, control system 102 may, upon receiving the first user input of the plurality of user inputs and the next user input of the plurality of user inputs from only one of the first user interface and the second user interface (e.g., from only one of scan room user interface 104 and control room user interface 106, etc.), determine from the plurality of operations, based on the first user input and the next user input, a first operation thereof and a next operation thereof that are associated, respectively, with the first user input and the next user input.

As shown in FIG. 3B, at step 356, process 300B includes controlling, according to the determination of the first operation and the next operation, a first user interface and a second user interface to display information associated with the first operation, the next operation, and a current operational state of a power injector system. For example, control system 102 may control, according to the determination of the first operation and the next operation, the first user interface and the second user interface (e.g., each of scan room user interface 104 and control room user interface 106, etc.) to display information associated with the first operation, the next operation, and a current operational state of the power injector system 100.

In some non-limiting embodiments or aspects, the current operational state of power injector system 100 is different than the first operation and the next operation.

In some non-limiting embodiments or aspects, control system 102 may control the first user interface to display the information associated with the first operation, the next operation, and the current operational state of the power injector system in a first visual layout, and control the second user interface to display the information associated with the first operation, the next operation, and the current operational state of the power injector system in a second visual layout different than the first visual layout. For example, control system 102 may control the first user interface and the second user interface to display the same information in different visual layouts.

Figure 3C:
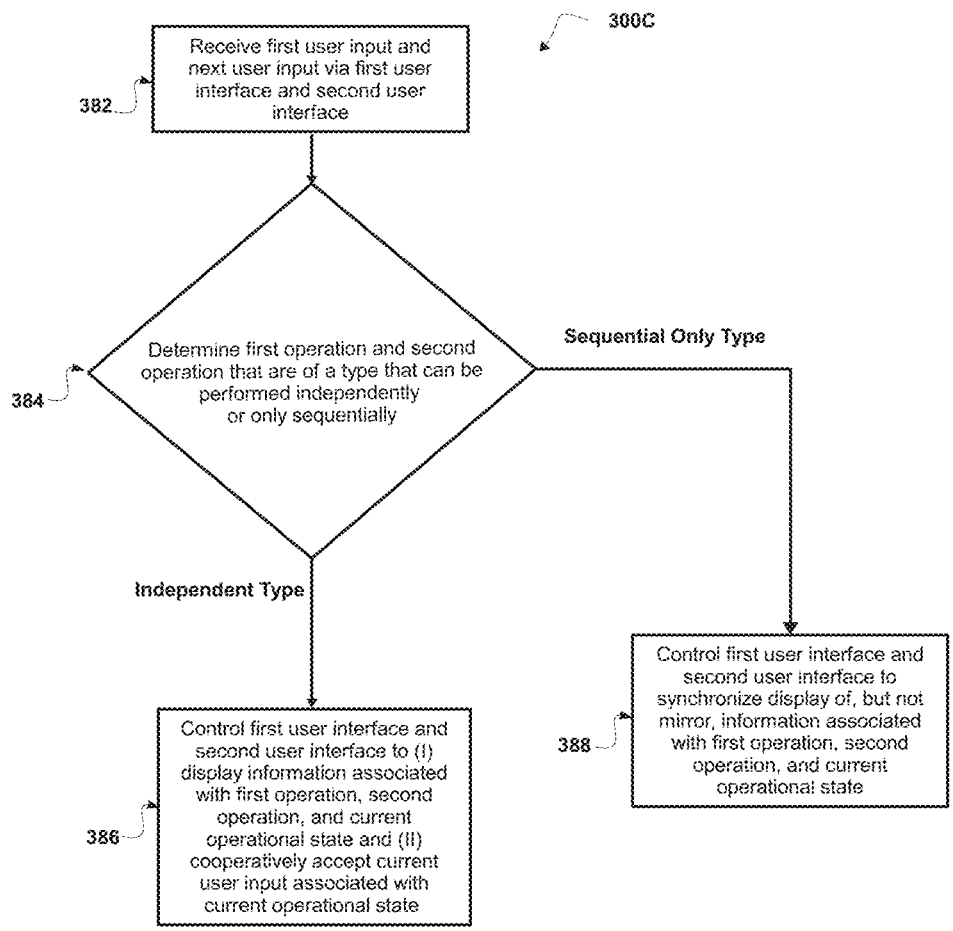
FIG. 3C is a flowchart of non-limiting embodiments or aspects of a process for providing independent user interfaces for operating a power injector system.

Referring now to FIG. 3C, FIG. 3C is a flowchart of non-limiting embodiments or aspects of a process 300C for providing independent user interfaces for operating a power injector system. In some non-limiting embodiments or aspects, one or more of the steps of process 300C are performed (e.g., completely, partially, etc.) by control system 102 (e.g., one or more devices of control system 102). In some non-limiting embodiments or aspects, one or more of the steps of process 300C are performed (e.g., completely, partially, etc.) by another device or a group of devices separate from or including control system 102, such as scan room user interface 104 (e.g., one or more devices of scan room user interface 104), control room user interface 106 (e.g., one or more devices of control room user interface 106), power injector 108 (e.g., one or more devices of power injector 108), and/or the like.

As shown in FIG. 3C, at step 382, process 300C includes receiving a first user input of a plurality of user inputs and a next user input of the plurality of user inputs from one of a first user interface and a second user interface and the other of the first user interface and the second user interface, respectively. For example, control system 102 may receive the first user input of a plurality of user inputs and the next user input of the plurality of user inputs from one of the first user interface and the second user interface and the other of the first user interface and the second user interface, respectively. As an example, the first user input of a plurality of user inputs and the next user input of the plurality of user inputs may be received by the first user interface and the second user interface and the other of the first user interface and the second user interface, respectively. In such an example, a user may include a single user traveling between the first user interface and the second user interface and/or a two separated users cooperatively operating the first user interface and the second user interface, respectively.

In some non-limiting embodiments or aspects, control system 102 may control one of the first user interface and the second user interface and the other of the first user interface and the second user interface to simultaneously accept the first user input of the plurality of user inputs and the next user input of the plurality of user inputs, respectively. In some non-limiting embodiments or aspects, control system 102 may control one of the first user interface and the second user interface to provide a prompt that requests a user to input the next user input based on the first user input received from the other of the first user interface and the second user interface. In some non-limiting embodiments or aspects, the first user input and the next user input may be associated with a same operational state of power injector system 100. In some non-limiting embodiments or aspects, the first user input and the next user input may be associated with different operational states of the power injector system. In some non-limiting embodiments or aspects, the current operational state of power injector system 100 is different than the first operation and the next operation.

In some non-limiting embodiments or aspects, control system 102 may control one of the first user interface and the second user interface and the other of the first user interface and the second user interface to prevent acceptance of the next user input and the first user input, respectively.

As shown in FIG. 3C, at step 384, process 300C includes upon receiving the first user input of the plurality of user inputs and the next user input of the plurality of user inputs from one of the first user interface and the second user interface and the other of the first user interface and the second user interface, respectively, determining that the first operation and the next operation associated, respectively, with the first user input and the next user input are of a type that can be performed independently or a type that can be performed only sequentially. For example, control system 102 may, upon receiving the first user input of the plurality of user inputs and the next user input of the plurality of user inputs from one of the first user interface and the second user interface and the other of the first user interface and the second user interface, respectively, determine that the first operation and the next operation associated, respectively, with the first user input and the next user input are of a type that can be performed independently or a type that can be performed only sequentially. As an example, control system 102 may determine that the first operation and the next operation associated, respectively, with the first user input and the next user input are of a type that can be performed independently or a type that can be performed only sequentially by comparing the first user input and the next user input to a look-up table and/or one or more rules defining operation types of operations or operational states of power injector system 100.

As shown in FIG. 3C, at step 386, process 300C includes upon determining that the first operation and the next operation associated, respectively, with the first user input and the next user input are of a type that can be performed independently, controlling, according to the determination (I) the first user interface and the second user interface to display the information associated with the first operation, the next operation, and the current operational state of the power injector system and (II) the first user interface and the second user interface to cooperatively accept current user input associated with the current operational state of the power injector system. For example, control system 102 may, upon determining that the first operation and the next operation associated, respectively, with the first user input and the next user input are of a type that can be performed independently, control, according to the determination (I) the first user interface and the second user interface to display the information associated with the first operation, the next operation, and the current operational state of the power injector system and (II) the first user interface and the second user interface to cooperatively accept current user input associated with the current operational state of the power injector system.

In some non-limiting embodiments or aspects, control system 102 may control the first user interface to display the information associated with the first operation, the next operation, and the current operational state of the power injector system in a first visual layout, and control the second user interface to display the information associated with the first operation, the next operation, and the current operational state of the power injector system in a second visual layout different than the first visual layout. For example, control system 102 may control the first user interface and the second user interface to display the same information in different visual layouts.

As shown in FIG. 3C, at step 388, process 300C includes upon determining that the first operation and the next operation associated, respectively, with the first user input and the next user input are of a type that can be performed only sequentially, controlling, according to the determination, the first user interface and the second user interface to synchronize display of, but not mirror, the information associated with the first operation, the next operation, and the current operational state of the power injector system. For example, control system 102 may, upon determining that the first operation and the next operation associated, respectively, with the first user input and the next user input are of a type that can be performed only sequentially, control, according to the determination, the first user interface and the second user interface to synchronize display of, but not mirror, the information associated with the first operation, the next operation, and the current operational state of the power injector system 100.

In some non-limiting embodiments or aspects, control system 102 may control the first user interface to display the information associated with the first operation, the next operation, and the current operational state of the power injector system in a first visual layout or form, and control the second user interface to display the information associated with the first operation, the next operation, and the current operational state of the power injector system in a second visual layout or form different than the first visual layout. For example, control system 102 may control the first user interface and the second user interface to display the same information in different visual layouts or forms.

Figure 4:
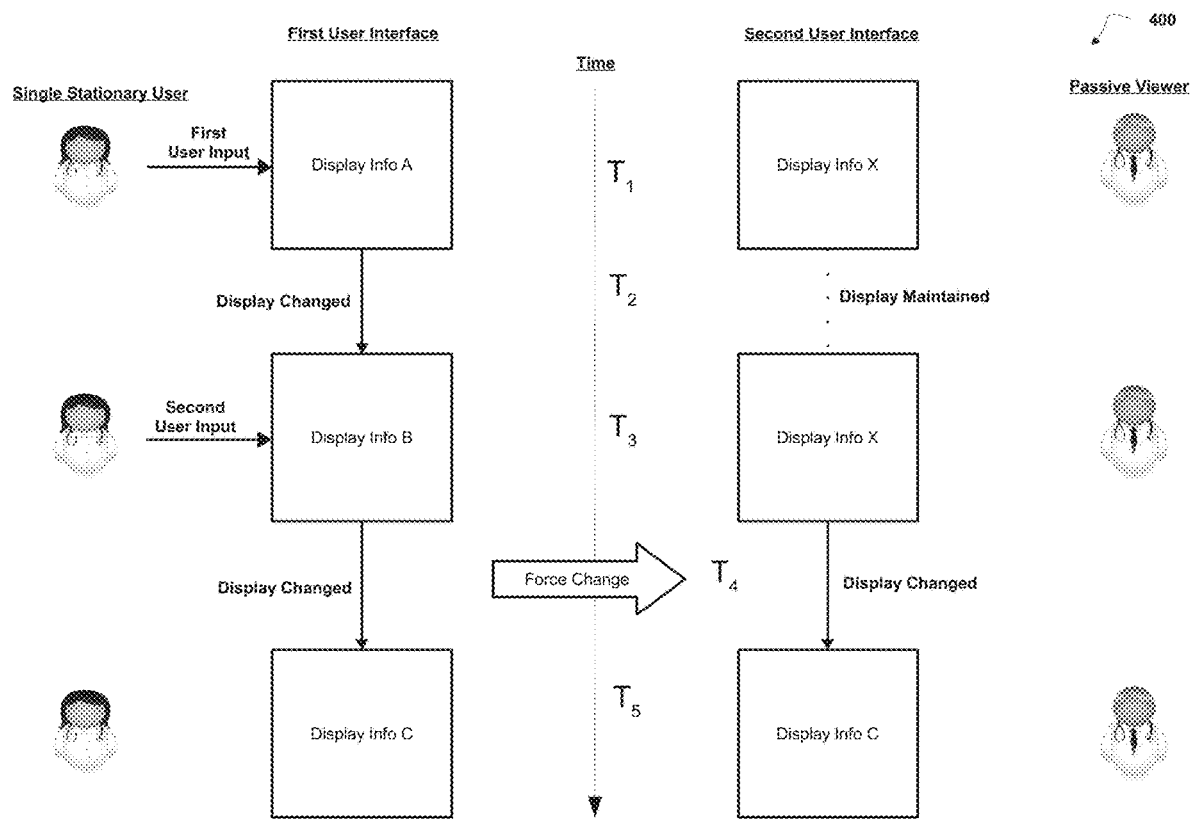
FIG. 4 is a diagram of an implementation of non-limiting embodiments or aspects of a process disclosed herein.

Referring now to FIG. 4, FIG. 4 is a diagram of non-limiting embodiments or aspects of an implementation 400 relating to a process for providing independent user interfaces for operating a power injector system. As shown at time $T_1$, a first user interface (e.g., scan room user interface 104 or control room user interface 106, etc.) may display information A and a second user interface may display information X different than information A. A single stationary user at the first user interface (e.g., a user at scan room user interface 104 or a user at control room user interface 106, etc.) may view the information A and input first user input to the first user interface. At the same time $T_1$, a passive viewer may view the information X at the second user interface (e.g., the other of scan room user interface 104 and control room user interface 106, etc.). As shown at time $T_2$, control system 102, based on the first user input, may control the first user interface to change and control the second user interface to maintain display of the information X. For example, control system 102 may control the first user interface to change the display to display information B and control the second user interface to maintain the display of the information X. As an example, control system 102 can independently control or drive the first user interface and the second user interface to provide different information according to a current operational state of the control system 102 and the first user input. As shown at time $T_3$, the first user interface may display the information B, which may be viewed by the single stationary user, and the second user interface may continue to display the information X, which may be different than the information B and viewed by the passive viewer.

As further shown at time $T_3$, the single stationary user may input a second user input to the first user interface, which is displaying the information B. As shown at time $T_4$, in response to the second user input, control system 102 may control the first user interface and the second user interface to change. For example, control system 102 may control the first user interface and the second user interface to change the respective displays thereof to display information C, which may be different than information A and information B. As an example, control system 102 can independently control or drive the first user interface and the second user interface, but synchronize at least a portion of the first graphical user interface and the second graphical user interface, for example, by transitioning or snapping the second graphical user interface to provide the same or similar information as the first user interface. For example, control system 102 may force the second graphical user interface to display the same information C, such as, information related to arming of power injector 108 in response to receipt of the second user input including an instruction to arm power injector 108. As shown at time $T_5$, each of the first user interface and the second may display the same information C, which may be viewed by the single stationary user and the passive viewer, respectively. For example, the passive viewer in the control room may be automatically notified of the arming of power injector 108 by the changing of control room user interface 106 to display information related thereto, and the single stationary viewer may receive a confirmation in response to an instruction to arm power injector 108 by the changing of control room user interface 106 to display the same information related to the arming of power injector 108.

Figure 5:
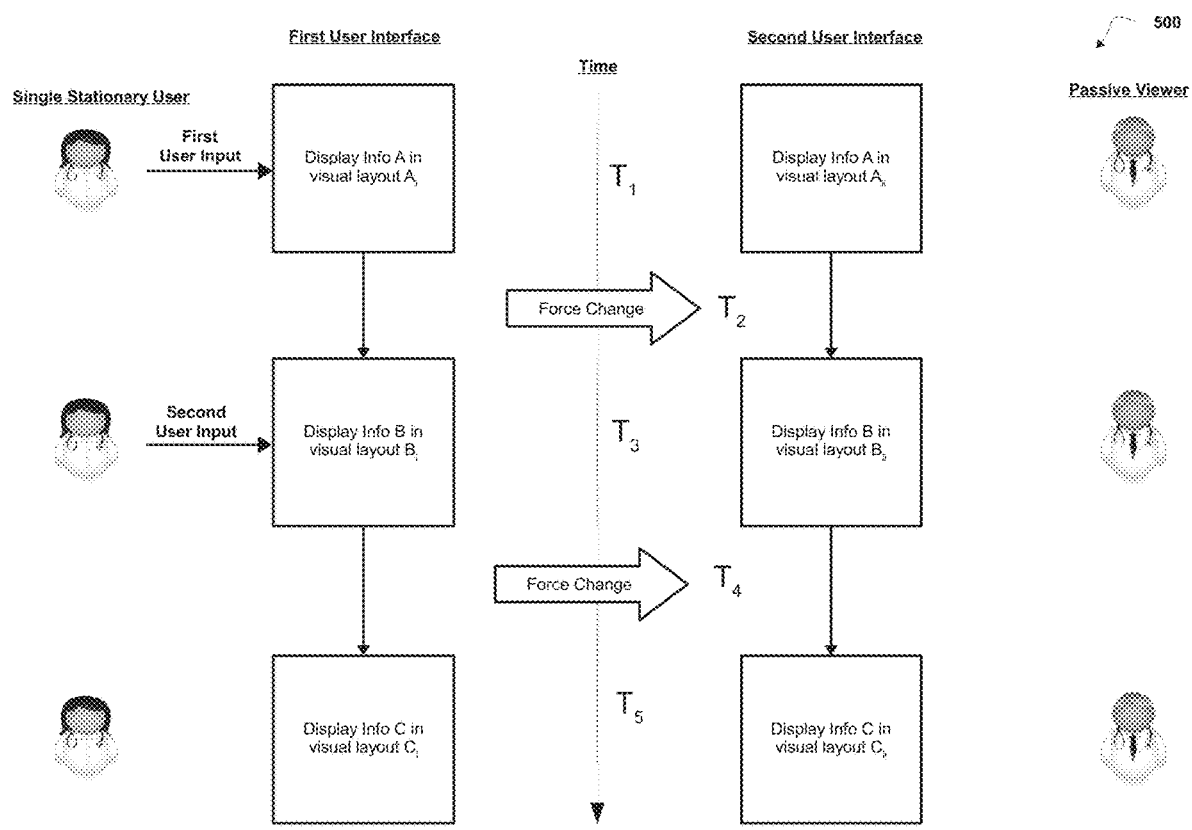
FIG. 5 is a diagram of an implementation of non-limiting embodiments or aspects of a process disclosed herein.

Referring now to FIG. 5, FIG. 5 is a diagram of non-limiting embodiments or aspects of an implementation 500 relating to a process for providing independent user interfaces for operating a power injector system. As shown at time $T_1$, a first user interface (e.g., scan room user interface 104 or control room user interface 106, etc.) may display information A in a visual layout or format $A_i$ and a second user interface (e.g., the other of scan room user interface 104 and control room user interface 106, etc.) may display the same information A in a different visual layout or format $A_{ii}$ than the visual layout or format A. A single stationary user at the first user interface (e.g., a user at scan room user interface 104 or a user at control room user interface 106, etc.) may view the information A in the first visual layout $A_i$ and input a first user input to the first user interface. At the same time $T_1$, a passive viewer may view the same information A in the different visual layout or format $A_{ii}$ at the second user interface. As shown at time $T_2$, in response to the first user input, control system 102 may control the first user interface and the second user interface to change. For example, control system 102 may control the first user interface and the second user interface to change the respective displays thereof to display information B, which may be different than the information A. As an example, control system 102 can independently control or drive the first user interface and the second user interface, but synchronize at least a portion of the first graphical user interface and the second graphical user interface, for example, by transitioning or snapping the second graphical user interface to provide the same or similar information as the first user interface. For example, control system 102 may force the second graphical user interface to display the same information B in response to receipt of the second user input; however, the same information B may be displayed in a first visual layout or format $B_i$ at the first user interface and in a second visual layout or format $B_{ii}$ at the second user interface that is different than the first visual layout or format. As shown at time $T_3$, each of the first user interface and the second user interface may display the same information B, but in different visual layouts or formats $B_i$ and $B_{ii}$ which may be viewed by the single stationary user and the passive viewer, respectively.

As further shown at time $T_3$, the single stationary user may input a second user input to the first user interface, which is displaying the information B. As shown at time $T_4$, in response to the second user input, control system 102 may control the first user interface and the second user interface to change. For example, control system 102 may control the first user interface and the second user interface to change the respective displays thereof to display information C, which may be different than information A and information B. As an example, control system 102 can independently control or drive the first user interface and the second user interface, but synchronize at least a portion of the first graphical user interface and the second graphical user interface, for example, by transitioning or snapping the second graphical user interface to provide the same or similar information as the first user interface. For example, control system 102 may force the second graphical user interface to display the same information C in response to receipt of the second user input; however, the same information C may be displayed in a first visual layout or format $C_i$ at the first user interface and in a second visual layout or format $C_{ii}$ at the second user interface that is different than the first visual layout or format. As shown at time $T_5$, each of the first user interface and the second user interface may display the same information C, which may be viewed by the single stationary user and the passive viewer, respectively.

Figure 6:
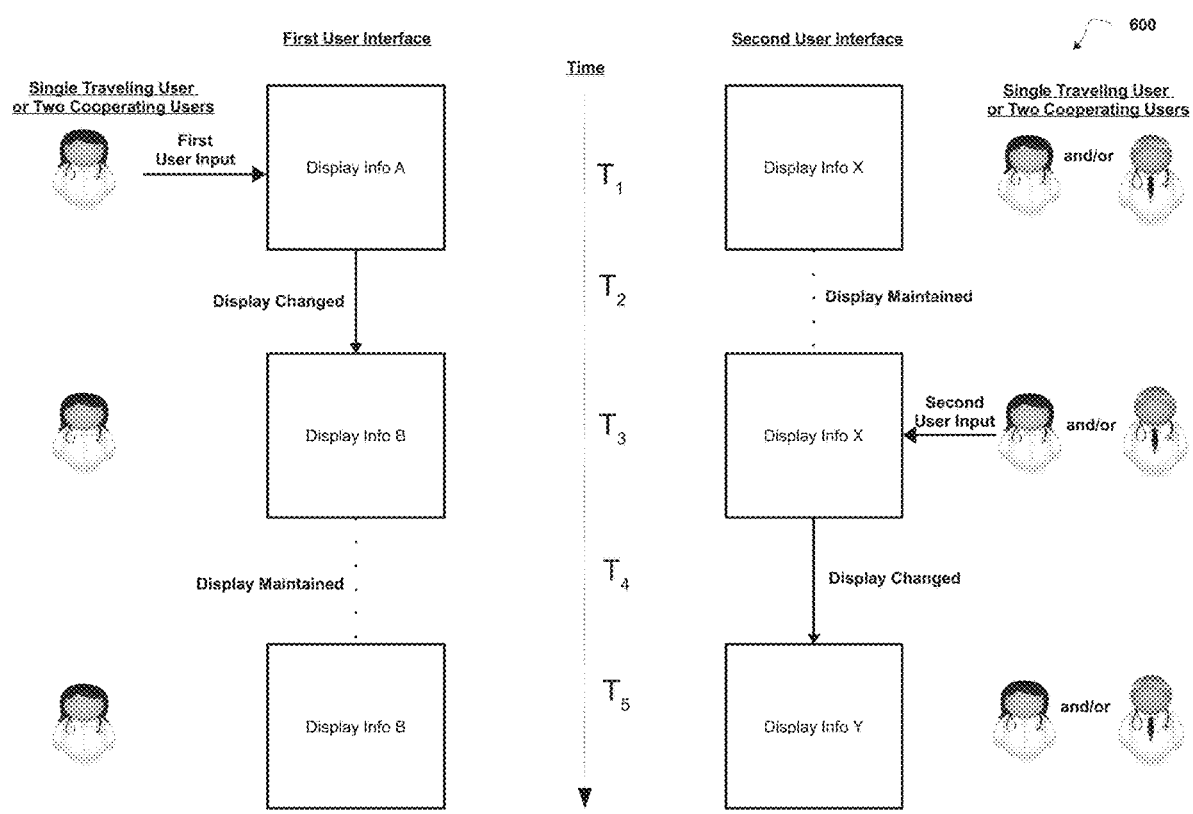
FIG. 6 is a diagram of an implementation of non-limiting embodiments or aspects of a process disclosed herein.

Referring now to FIG. 6, FIG. 6 is a diagram of non-limiting embodiments or aspects of an implementation 600 relating to a process for providing independent user interfaces for operating a power injector system. As shown at time $T_1$, a first user interface (e.g., scan room user interface 104 or control room user interface 106, etc.) may display information A and a second user interface may display information X different than information A. A single traveling user or a first cooperating user at the first user interface (e.g., a user at scan room user interface 104 or a user at control room user interface 106, etc.) may view the information A and input a first user input to the first user interface. At the same time $T_1$, the single traveling user or a cooperating user may view the information X at the second user interface (e.g., the other of scan room user interface 104 and control room user interface 106, etc.). As shown at time $T_2$, control system 102, based on the first user input, may control the first user interface to change and control the second user interface to maintain display of the information X. For example, control system 102 may control the first user interface to change the display to display information B and control the second user interface to maintain the display of the information X. As an example, control system 102 can independently control or drive the first user interface and the second user interface to provide different information according to a current operational state of the control system 100 and the first user input. As shown at time $T_3$, the first user interface may display the information B, which may be viewed by the single stationary user or the first cooperating user, and the second user interface may continue to display the information X, which may be different than the information B and viewed by the single traveling user or the second cooperating user.

As further shown at time $T_3$, the single traveling user or the second cooperating user may input a second user input to the second user interface, which is displaying the information X. As shown at time $T_4$, in response to the second user input, control system 102, based on the second user input, may control the second user interface to change and control the first user interface to maintain display of the information B. For example, control system 102 may control the second user interface to change the display to display information Y and control the first user interface to maintain the display of the information B. As an example, control system 102 can independently control or drive the first user interface and the second user interface to provide different information according to a current operational state of the control system 100 and the first user input. As shown at time $T_5$, the first user interface may continue to display the information B, which may be viewed by the single traveling user or the first cooperating user, and the second user interface may display the information Y, which may be different than the information B and the information X, and which may be viewed by the single traveling user or the second cooperating user. As an example, the information A and the information B may be associated with an operation for pre-loading power injector 108 with syringes in a scan room at scan room user interface 104, and the information X and the information Y may be associated with inputting a protocol for power injector 108 in a control room at control room user interface 106.

Figure 7:
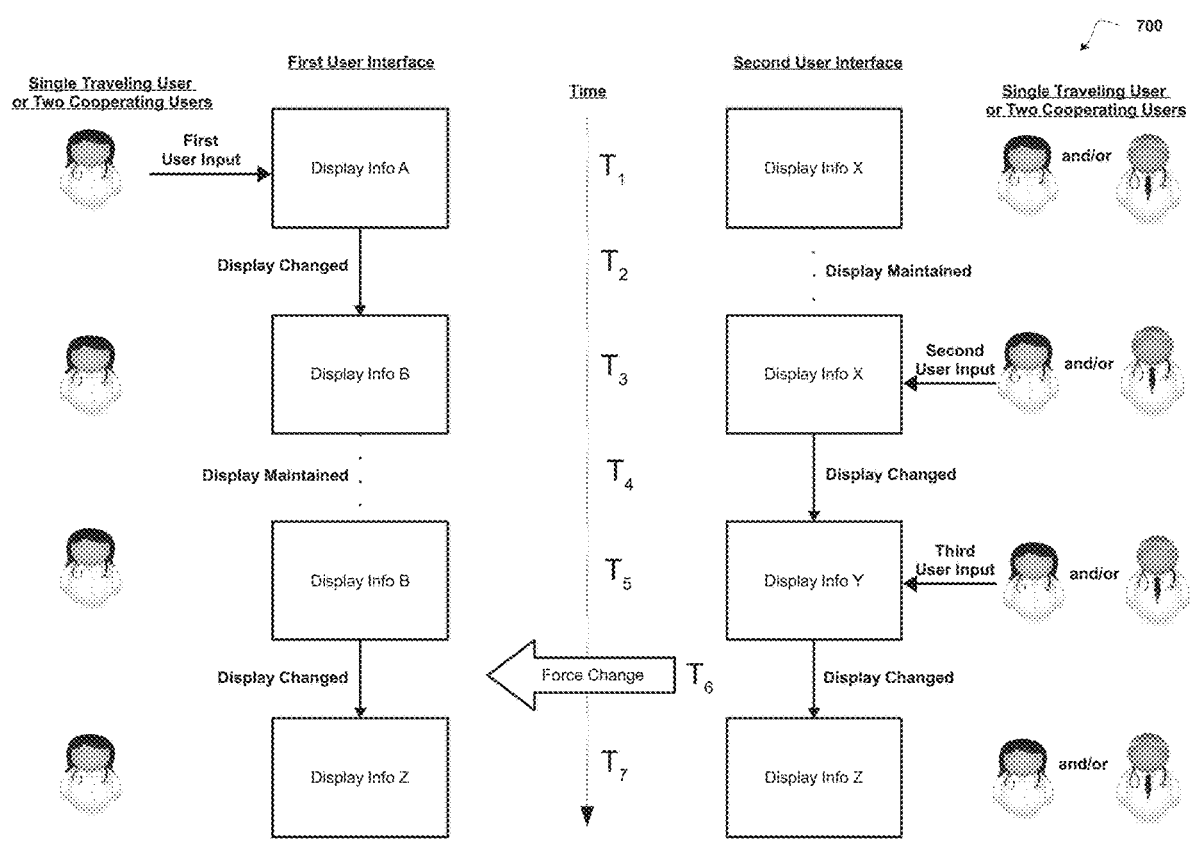
FIG. 7 is a diagram of an implementation of non-limiting embodiments or aspects of a process disclosed herein.

Referring now to FIG. 7, FIG. 7 is a diagram of non-limiting embodiments or aspects of an implementation 700 relating to a process for providing independent user interfaces for operating a power injector system. As shown at time $T_1$ a first user interface (e.g., scan room user interface 104 or control room user interface 106, etc.) may display information A and a second user interface may display information X different than information A. A single traveling user or a first cooperating user at the first user interface (e.g., a user at scan room user interface 104 or a user at control room user interface 106, etc.) may view the information A and input a first user input to the first user interface. At the same time $T_1$, the single traveling user or a second cooperating user may view the information X at the second user interface (e.g., the other of scan room user interface 104 and control room user interface 106, etc.). As shown at time $T_2$, control system 102, based on the first user input, may control the first user interface to change and control the second user interface to maintain display of the information X. For example, control system 102 may control the first user interface to change the display to display information B and control the second user interface to maintain the display of the information X. As an example, control system 102 can independently control or drive the first user interface and the second user interface to provide different information according to a current operational state of the control system 100 and the first user input. As shown at time $T_3$, the first user interface may display the information B, which may be viewed by the single traveling user or the first cooperating user, and the second user interface may continue to display the information X, which may be different than the information B, and which may be viewed by the single traveling user or the second cooperating user.

As further shown at time $T_3$, the single traveling user or the second cooperating user may input a second user input into the second user interface, which is displaying the information X. As shown at time $T_4$, in response to the second user input, control system 102, based on the second user input, may control the second user interface to change and control the first user interface to maintain display of the information B. For example, control system 102 may control the second user interface to change the display to display information Y and control the first user interface to maintain the display of the information B. As an example, control system 102 can independently control or drive the first user interface and the second user interface to provide different information according to a current operational state of the control system 100 and the first user input. As shown at time $T_5$, the first user interface may continue to display the information B, which may be viewed by the single traveling user or the first cooperating user, and the second user interface may display the information Y, which may be different than the information B and the information X, and which may be viewed by the single traveling user or the second cooperating user.

As further shown at time $T_5$, the single traveling user or the second cooperating user may input a third user input to the second user interface, which is displaying the information Y. As shown at time $T_6$, in response to the third user input, control system 102 may control the first user interface and the second user interface to change. For example, control system 102 may control the first user interface and the second user interface to change the respective displays thereof to display information Z, which may be different than information A, information B, information X and information Y. As an example, control system 102 can independently control or drive the first user interface and the second user interface, but synchronize at least a portion of the first graphical user interface and the second graphical user interface, for example, by transitioning or snapping the first graphical user interface to provide the same or similar information as the second user interface. For example, control system 102 may force the first graphical user interface to display the same information Z, such as, information related to arming of power injector 108 in response to receipt of the third user input including an instruction to arm power injector 108. As shown at time $T_7$, each of the first user interface and the second user interface may display the same information Z, which may be viewed by the single traveling user or first cooperating user and the single traveling user or second cooperating user, respectively.

Figure 8:
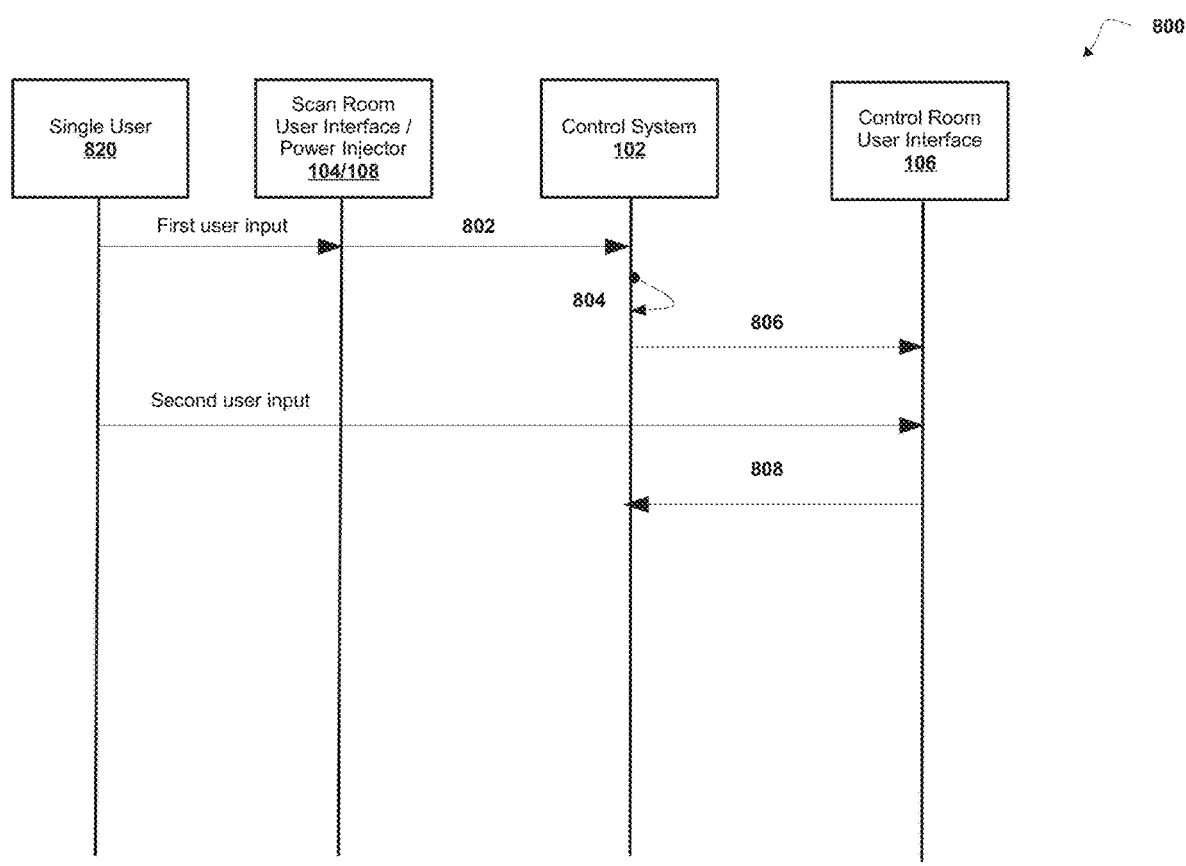
FIG. 8 is a diagram of an implementation of non-limiting embodiments or aspects of a process disclosed herein.

Referring now to FIG. 8, FIG. 8 is a diagram of non-limiting embodiments or aspects of an implementation 800 relating to a process for providing independent user interfaces for operating a power injector system. As shown at reference number 802, control system 102 receives first user input, via scan room user interface 104 from single user 820, associated with an operation for arming power injector 108. At reference number 804, control system 102 determines the operation for arming power injector 108 is associated with scan room user interface 104. At reference number 806, control system 102 controls control room user interface 106 to display an indication that power injector 108 is armed and graphics for performing a next sequential operation in a process for operating power injector system 100 based on the determined operation. In some non-limiting embodiments or aspects, the graphics for performing the next sequential operation may only be available via control room user interface 106. At reference number 808, control system 102, receives second user input, via control room user interface 106 from single user 820, associated with the next sequential operation. Accordingly, the indication that power injector 108 is armed and the controls for performing the next sequential operation are already available when single user 820 arrives at control room user interface 106 after traveling from scan room user interface 104.

Figure 9:
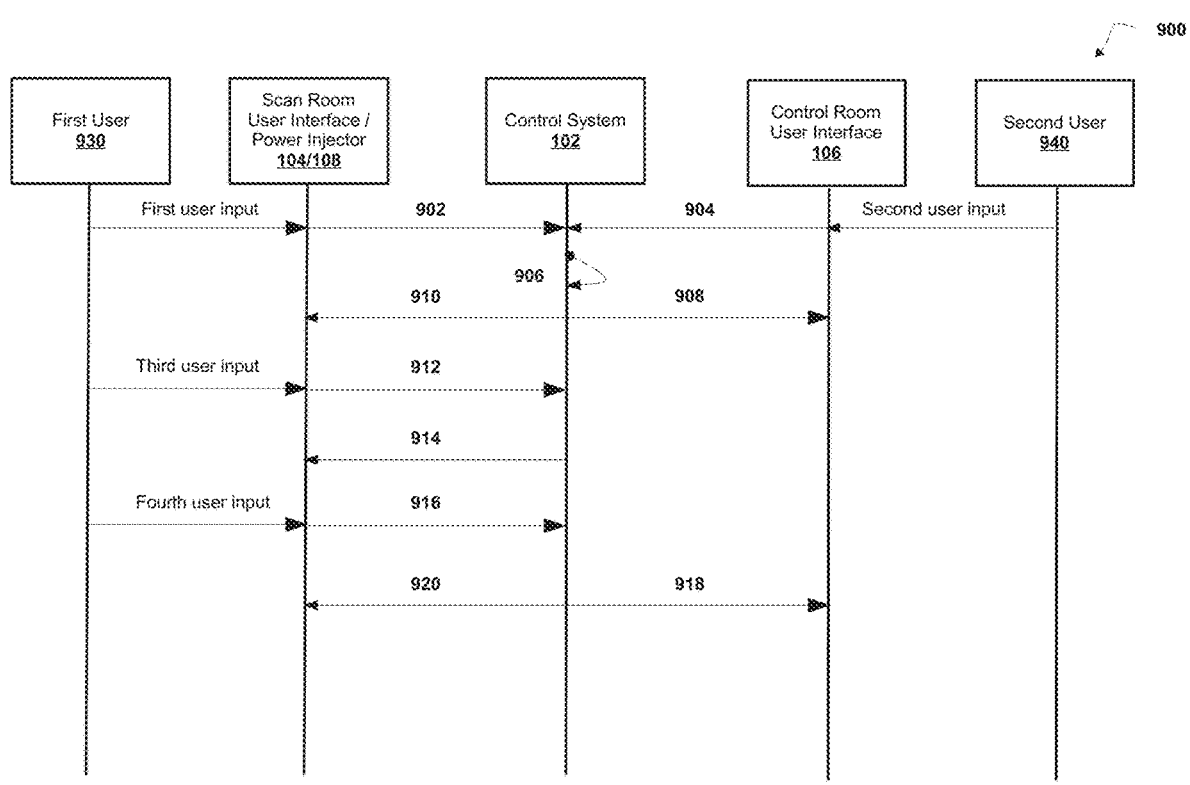
FIG. 9 is a diagram of an implementation of non-limiting embodiments or aspects of a process disclosed herein.

Referring now to FIG. 9, FIG. 9 is a diagram of non-limiting embodiments or aspects of an implementation 900 relating to a process for providing independent user interfaces for operating a power injector system. As shown at reference number 902, control system 102 receives first user input, via scan room user interface 104 from first user 930, associated with a fluid loading operation while simultaneously receiving, at reference number 904, second user input, via control room user interface 106 from a second user 940, associated with a patient and/or procedure setup operation. At reference number 906, control system 102 determines the fluid loading operation is associated with scan room user interface 104 and the patient and/or procedure setup operation is associated with control room user interface 106. At reference number 908, control system 102 controls control room user interface 106 to include information associated with the fluid loading operation currently being performed via scan room user interface 104 (e.g., a progress or status indicator, fluid identification information, etc.), and at reference number 910 control system 102 control scan room user interface 104 to include information associated with the patient and/or procedure setup operation (e.g., a progress or status indicator, patient information, procedure information, etc.). For example, a fluid loading operation can be independent from a patient and/or procedure setup operation, and first user 930 can view a progress and/or information associated with the patient and/or procedure setup operation being performed at via control room user interface 106 by second user 940 at the same time second user 940 can view a progress and/or information associated with the fluid loading operation being performed at scan room user interface 104 by first user 930. At reference number 912, control system 102 receives third user input, via scan room user interface 104 from first user 930, including a request to edit patient and/or procedure data associated with the patient and/or procedure setup operation. At reference number 914, control system 102 controls scan room user interface 104 to provide a display for editing the patient and/or procedure data, for example, a display including patient and/or procedure data received via control room user interface 106. At reference number 916, control system 102 receives fourth user input, via scan room user interface 104 from first user 930, including edits to the patient and/or procedure data. At reference number 918, control system 102 controls control room user interface 106 to update the patient and/or procedure data based on the fourth user input, and at reference number 920, control system 102 controls scan room user interface 104 to update the patient and/or procedure data based on the fourth user input. Accordingly, first user 930 performing a fluid loading operation at scan room user interface 104 can be notified of second user 940 performing a patient and/or procedure setup operation at control room user interface 106 and/or patient and/or procedure information associated therewith and, if desirable, first user 930 can switch scan room user interface 104 to be associated with and/or perform the patient and/or procedure setup operation, for example, while the system is filling fluids loaded by first user 930 during the fluid loading operation.

Figure 10:
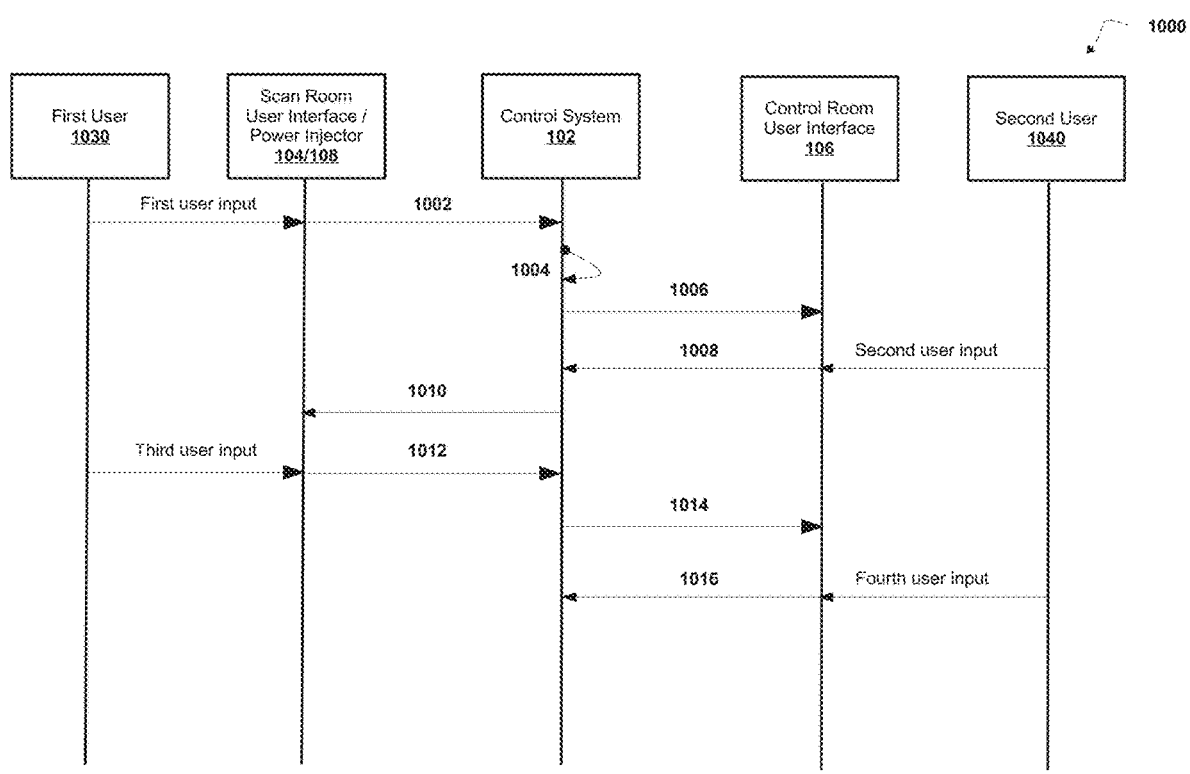
FIG. 10 is a diagram of an implementation of non-limiting embodiments or aspects of a process disclosed herein.

Referring now to FIG. 10, FIG. 10 is a diagram of non-limiting embodiments or aspects of an implementation 1000 relating to a process for providing independent user interfaces for operating a power injector system at reference number 1002, control system 102 receives first user input, via scan room user interface 104 from first user 1030, associated with a patient and/or procedure setup operation. At reference number 1004, control system 102 determines the patient and/or procedure setup operation is associated with scan room user interface 104. At reference number 1006, control system 102 controls control room user interface 106 to provide a display for editing the patient and/or procedure data, for example, a display including patient and/or procedure data received via scan room user interface 104. At reference number 1008, control system 102 receives second user input, via control room user interface 106 from second user 1040, associated with the patient and/or procedure setup operations, such as, edits to an injection protocol and an instruction to arm power injector 108. At reference number 1010, control system 102 controls scan room user interface 104 to update the patient and/or procedure data based on the second user input, for example, to include an indication that the power injector 108 is armed and a display associated with a next sequential operation, such as an operation to start the injection at scan room user interface 104. At reference number 1012, control system 102 receives third user input, via scan room user interface 104 from first user 1030, including an instruction to start the injection, for example, an instruction to start a test injection while palpating a catheter site, etc. At reference number 1014, control system 102 controls control room user interface 106 to include an indication that the injection has been initiated, while providing a display associated with one or more operations for performing scanner acquisitions and/or initiating any remaining contrast injections at control room user interface 106, and at reference number 1016, control system 102 receives fourth user input, via control room user interface 104 from second user 1040, for completing a process for operating power injector system 100.

In some non-limiting embodiments or aspects, control system 102 controls a user interface based on a location (e.g., a location, a proximity, a type of user interface, etc.) of the user interface with respect to power injector 108. For example, control system 102 can control scan room user interface 104 with respect to an operation of power injector system 100 in a different manner than control room user interface 106 with respect to the same operation of power injector system 100. As an example, control system 102 can control scan room user interface 104 to display in a visually more predominate manner information associated with an operation currently associated with scan room user interface 104, while controlling control room user interface 106 to display in a less visually predominate manner the same or similar information, and/or vice-versa.

In some non-limiting embodiments or aspects, an operation of power injector system 100 is associated with one or more constraints on one or more user interfaces in power injector system 100. For example, control system 102 can inhibit or prevent user input associated with one or more operations from being received at a user interface, inhibit or prevent a GUI associated with one or more operations from being displayed at a user interface, inhibit or prevent one or more operations of power injector system 100 from being initiated or executed at a user interface, and/or the like based on one or more constraints on the user interface that are associated with the one or more operations. As an example, in some non-limiting embodiments or aspects, scan room user interface 104 and control room user interface 106 share a set of common operations that can be performed at either location (e.g., patient/procedure setup, injection protocol setup, exam execution and injection monitoring, etc.), and each of scan room user interface 104 and control room user interface 104 is associated with one or more unique operations that may be performed only at that location (e.g. fluid loading at scan room user interface 104, protocol management at control room user interface 106, etc.).

In some non-limiting embodiments or aspects, an operation of power injector system 100 is associated with one or more constraints on one or more other operations at one or more user interfaces in power injector system 100. For example, control system 102 can inhibit or prevent one or more other operations from being associated with (e.g., being performed at, providing a display associated with at, receiving input associated with, etc.) one or more user interfaces (e.g., scan room user interface 104, control room user interface 106, etc.) based on an operation associated with one or more constraints on the one or more other operations, for example, based on the operation associated with the one or more constraints on the one or more other operations being performed at a same time as the one or more other operations, having already been performed (e.g., completed, etc.) before the one or more other operations, and/or the like. For example, control system 102 can inhibit or prevent user input associated with one or more other operations from being received at a user interface, inhibit or prevent a GUI associated with one or more other operations from being displayed at a user interface, inhibit or prevent one or more other operations from being initiated or executed at a user interface, and/or the like based on an operation associated with one or more constraints on the one or more other operations. As an example, control system 102 can prevent user input from initiating or executing an operation of power injector system 100, prevent a GUI associated with initiating or executing an operation of power injector system 100 from being displayed, and/or prevent initiation or execution of an operation of power injector system 100 at scan room user interface 104 and/or control room user interface 106 based on a determination that a conflicting operation is currently in process and/or has not been transitioned from the user interface at which the conflicting operation was initiated (e.g., based on user input associated with parameters of the conflicting operation being received via a user interface and/or having not yet been received via a user interface after beginning the conflicting operation, etc.). As an example, control system 102 can prevent user input from initiating or executing a report review process at control room user interface 106 based on a determination that power injector 108 is currently delivering an injection.

Figure 11:
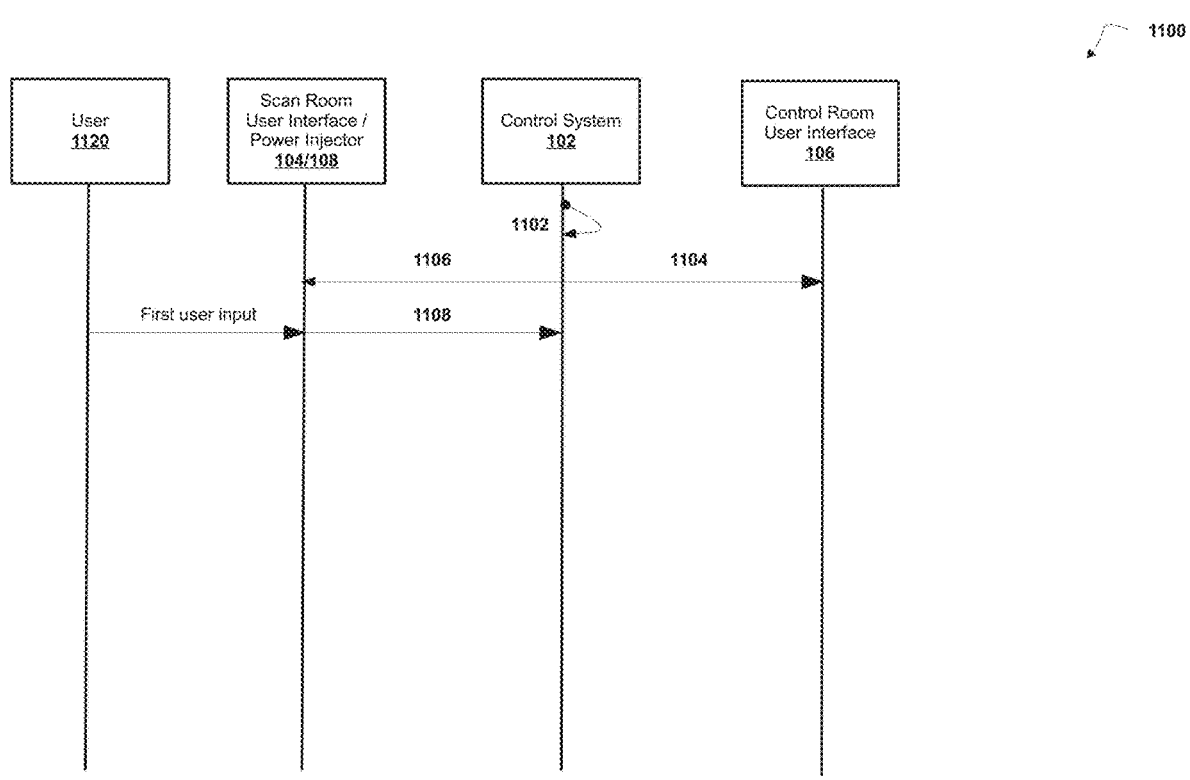
FIG. 11 is a diagram of an implementation of non-limiting embodiments or aspects of a process disclosed herein.

Referring now to FIG. 11, FIG. 11 is a diagram of non-limiting embodiments or aspects of an implementation 1100 relating to a process for providing independent user interfaces for operating a power injector system. As shown at reference number 1102, control system 102 can determine that air has been detected in power injector 108 (e.g., in one or more syringes and/or associated tubing set(s) used therewith, etc.) during an injection. At reference number 1104, control system 102 controls control room user interface 106 to provide a notification that air has been detected in power injector 108 and a prompt that requests a user to initiate an operation to clear the air at scan room user interface 104 and, at reference number 1106, controls scan room user interface 104 to provide a display associated with an operation to clear the air. For example, control system 102 may not allow an operation to clear the air from power injector 108 to be performed and/or initiated at control room user interface 106. At reference number 1108, control system 102 receives first user input, via scan room user interface 104 from user 1120, associated with the operation to clear the air. Accordingly, power injector system 100 can ensure a presence of the user (e.g., a Radiologist, Technologist or other medical personnel) at the side of a patient in the scan room to disconnect and purge the patient line or other affected tubing instead of the user inadvertently clicking through buttons in the control room while the patient is connected and injecting air. In some non-limiting embodiments or aspects, an operation for identifying fluids that are being loaded into power injector 108 must be performed at scan room user interface 104 (via, e.g., a barcode reader, RFID tag reader or other means) to ensure that the fluid that is spiked in a given location is labeled correctly on scan room user interface 104 for later selection.

In some non-limiting embodiments or aspects, user input is associated with a hierarchy of user input (e.g., a hierarchy of commands, etc.). For example, first user input associated with a first user interface and/or a first operation can be ranked higher or lower in a hierarchy of user input than second user input associated with a second user interface and/or a second operation. As an example, first user input associated with a first user interface and/or a first operation can be adjusted, modified, or overruled based on second user input associated with a second user interface and/or a second operation. In some non-limiting embodiments or aspects, control system 102 can adjust, modify, or overrule first user input associated with a first operation received via a first user interface based on second user input associated with the first operation received via a second user interface. For example, user input or commands received via the second user interface can be ranked higher in the hierarchy of user input than user input or commands received via the first user interface. In some non-limiting embodiments or aspects, control system 102 can adjust, modify, or overrule first user input associated with a first operation based on second user input associated with a second operation. For example, user input or commands associated with a second operation can be ranked higher in the hierarchy of user input than user input or commands associated with a first operation.

In some non-limiting embodiments or aspects, control system 102 controls the first user interface based on information associated with a first patient, and controls the second user interface based on information associated with a second patient different than the first patient. For example, it may be convenient for a first user in a control room to prepare power injector system 100 for a next patient by performing a patient and/or procedure setup operation at control room user interface 106 at a same time that a previous patient is still within the scan room, e.g., still being scanned, and/or the like. As an example, this pre-entry of patient data is especially advantageous in a case of delayed imaging, where a scan can occur minutes after an injection is complete. Control system 102 can control control room user interface 106 to include a display associated with the patient and/or procedure setup operation, and control scan room user interface 104 to include a generic display (e.g., a home screen display, etc.) that does not disclose information associated with the next patient in the scan room. If scan room user interface 104 and control room user interface 106 were mirrored exactly, patient data would be displayed in the scan room to an unrelated patient and, to protect privacy, a user would have to wait until the unrelated patient has left the scan room to enter information for the next patient. Accordingly, power injector system 100 can enable independent user interfaces where scan room user interface 104 does not display data associated with a next patient, e.g., the scan room remains on the home screen after the patient's exam has ended, thereby not exposing what a user in the control room is doing until user input associated with an arrival of the next patient in the scan room is received via scan room user interface 104 and/or control room user interface 106.

In some non-limiting embodiments or aspects, if control room user interface 106 loses communications with scan room user interface 104 (and/or control system 102), control room user interface 106 automatically displays a predetermined home screen that includes an indication of a communications loss, and scan room user interface 104 continues to operate in a normal manner for operating power injector system 100. When communications between scan room user interface 104 and control room user interface 106 (and/or control system 102) is reestablished, control room user interface 106 resumes operating in a normal manner for operating power injector system 100.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A power injector system comprising:
    a power injector configured to deliver fluid to a patient in an injection procedure;
    a first user interface;
    a second user interface; and
    a computer system comprising one or more processors, wherein the computer system is programmed or configured to:
    receive, via the first user interface, a first user input;
    determine a first operation of the power injector system that is associated with the first user interface based on the first user input;
    control the second user interface based on the first operation associated with the first user interface, wherein the first user interface is proximate the power injector in a scan room, and wherein the second user interface is remote from the power injector in a control room;
    control the first user interface based on information associated with a first patient; and
    simultaneously control the second user interface based on information associated with a second patient different than the first patient by performing a patient and/or procedure setup operation for the second patient at the second user interface in the control room to prepare the power injector for the second patient at a same time that the first patient is within the scan room, wherein the first user interface does not disclose the information associated with the second patient.

2. The power injector system of claim 1, wherein the first user interface includes a first graphical user interface, wherein the second user interface includes a second graphical user interface, and wherein the computer system is further programmed or configured to:
    control the first graphical user interface to display information associated with the first user input in a first visual layout; and
    control the second graphical user interface to display the information associated with the first user input in a second visual layout different than the first visual layout.

3. The power injector system of claim 1, wherein the computer system is further programmed or configured to:
    control the second user interface based on a location of the second user interface with respect to the power injector.

4. The power injector system of claim 1, wherein the computer system is further programmed or configured to:
    receive a second user input simultaneously with receiving the first user input via the first user interface.

5. The power injector system of claim 4, wherein the first user input and the second user input are associated with a same operation of the power injector system.

6. The power injector system of claim 4, wherein the first user input is associated with the first operation of the power injector system, and wherein the second user input is associated with a second operation of the power injector system different than the first operation of the power injector system.

7. The power injector system of claim 1, wherein the computer system is further programmed or configured to:
    control the second user interface to prevent input of a second user input via the second user interface.

8. The power injector system of claim 4 wherein the computer system is further programmed or configured to:
    receive, via the second user interface, a third user input, wherein the third user input is associated with a different operation of the power injector system than the second user input.

9. The power injector system of claim 1, wherein the computer system is further programmed or configured to:
    control the second user interface to provide a prompt that requests a user to input a second user input via the first user interface.

10. A computer program product for use in operating a power injector system, wherein the power injector system includes a first user interface, a second user interface, at least one processor, and a power injector for delivering fluid to a patient, the computer program product comprising at least one non-transitory computer-readable medium including program instructions that, when executed by the at least one processor, cause the at least one processor to:
    receive, via the first user interface, a first user input;
    determine a first operation of the power injector system that is associated with the first user interface based on the first user input;
    control the second user interface based on the first operation associated with the first user interface, wherein the first user interface is proximate the power injector in a scan room, and wherein the second user interface is remote from the power injector in a control room;
    control the first user interface based on information associated with a first patient; and simultaneously control the second user interface based on information associated with a second patient different than the first patient by performing a patient and/or procedure setup operation for the second patient at the second user interface in the control room to prepare the power injector for the second patient at a same time that the first patient is within the scan room, wherein the first user interface does not disclose the information associated with the second patient.

11. The computer program product of claim 10, wherein the first user interface includes a first graphical user interface, wherein the second user interface includes a second graphical user interface, wherein the program instructions further cause the at least one processor to:
control the first graphical user interface to display information associated with the first user input in a first visual layout; and
control the second graphical user interface to display the information associated with the first user input in a second visual layout different than the first visual layout.

12. The computer program product of claim 10, wherein the control of the second user interface includes controlling the second user interface based on a location of the second user interface with respect to the power injector.

13. The computer program product of claim 10, wherein the program instructions further cause the at least one processor to:
receive, via the second user interface, a second user input simultaneously with the receiving of the first user input via the first user interface.

14. The computer program product of claim 13, wherein the first user input and the second user input are associated with a same operation of the power injector system.

15. The computer program product of claim 13, wherein the first user input is associated with the first operation of the power injector system, and wherein the second user input is associated with a second operation of the power injector system different than the first operation of the power injector system.

16. The computer program product of claim 10, wherein the control of the second user interface includes controlling the second user interface to prevent input of a second user input via the second user interface.

17. The computer program product of claim 13, wherein the program instructions further cause the at least one processor to:
receive, via the second user interface, a third user input, wherein the third user input is associated with a different operation of the power injector system than the second user input.

18. The computer program product of claim 10, wherein the control of the second user interface includes controlling the second user interface to provide a prompt that requests a user to input a second user input via the first user interface.

19. A method for providing independent user interfaces for operating a power injector system, wherein the power injector system includes a first user interface, a second user interface, and a power injector for delivering fluid to a patient, the method comprising:
receiving, via the first user interface with a computer system including one or more processors, a first user input;
determining, with the computer system, a first operation of the power injector system that is associated with the first user interface based on the first user input;
controlling, with the computer system, the second user interface based on the first operation associated with the first user interface, wherein one of the first user interface is proximate the power injector in a scan room, and wherein the second user interface is remote from the power injector in a control room;
controlling, with the computer system, the first user interface based on information associated with a first patient; and
simultaneously controlling, with the computer system, the second user interface based on information associated with a second patient different than the first patient by performing a patient and/or procedure setup operation for the second patient at the second user interface in the control room to prepare the power injector for the second patient at a same time that the first patient is within the scan room, wherein the first user interface does not disclose the information associated with the second patient.

* * * * *

UNITED STATES PATENT AND TRADEMARK OFFICE
CERTIFICATE OF CORRECTION

| | |
|---|---|
| PATENT NO. | : 11,931,555 B2 |
| APPLICATION NO. | : 17/386897 |
| DATED | : March 19, 2024 |
| INVENTOR(S) | : Volkar et al. |

It is certified that error appears in the above-identified patent and that said Letters Patent is hereby corrected as shown below:

In the Specification

In Column 11, Line 65, delete "clause 21-25," and insert -- clauses 21-25, --, therefor.
In Column 16, Line 19, delete "difficultly" and insert -- difficulty --, therefor.
In Column 23, Line 67, delete "operation simultaneously" and insert -- operation --, therefor.
In Column 29, Line 57, delete "A. A" and insert -- $A_i$. A --, therefor.
In Column 31, Lines 6-7, delete "control system 100" and insert -- control system 102 --, therefor.
In Column 31, Line 28, delete "control system 100" and insert -- control system 102 --, therefor.
In Column 32, Line 1, delete "100" and insert -- 102 --, therefor.
In Column 32, Line 22, delete "control system 100" and insert -- control system 102 --, therefor.
In Column 34, Lines 41-42, delete "control room user interface 104" and insert -- control room user interface 106 --, therefor.
In Column 35, Lines 9-10, delete "control room user interface 104" and insert -- control room user interface 106 --, therefor.

In the Claims

In Column 40, Line 26, in Claim 19, delete "one of the first" and insert -- the first --, therefor.

Signed and Sealed this
Fourteenth Day of May, 2024

Katherine Kelly Vidal
*Director of the United States Patent and Trademark Office*